(12) United States Patent
Wang et al.

(10) Patent No.: US 8,003,604 B2
(45) Date of Patent: *Aug. 23, 2011

(54) HEPATITIS C VIRUS INHIBITORS

(75) Inventors: Alan Xiangdong Wang, Guilford, CT (US); Barbara Zhizhen Zheng, Cheshire, CT (US); Stanley D'Andrea, Wallingford, CT (US); Nicholas A. Meanwell, East Hampton, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 173 days.

This patent is subject to a terminal disclaimer.

(21) Appl. No.: 11/939,753

(22) Filed: Nov. 14, 2007

(65) Prior Publication Data

US 2008/0159982 A1    Jul. 3, 2008

Related U.S. Application Data

(60) Provisional application No. 60/866,120, filed on Nov. 16, 2006.

(51) Int. Cl.
A61K 38/00    (2006.01)

(52) U.S. Cl. ........................................................ 514/3.7

(58) Field of Classification Search .................. None
See application file for complete search history.

(56) References Cited

U.S. PATENT DOCUMENTS

| | | | |
|---|---|---|---|
| 5,223,432 A | 6/1993 | Wirz et al. | |
| 2005/0119168 A1* | 6/2005 | Venkatraman et al. | 514/9 |
| 2005/0153877 A1 | 7/2005 | Miao et al. | |
| 2005/0153900 A1* | 7/2005 | Velazquez et al. | 514/18 |
| 2005/0164921 A1* | 7/2005 | Njoroge et al. | 514/9 |
| 2006/0172950 A1 | 8/2006 | Wang et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0032936 A1 | 2/2008 | Gai et al. | |
| 2008/0039375 A1 | 2/2008 | Moore et al. | |
| 2008/0039470 A1 | 2/2008 | Niu et al. | |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |

(Continued)

OTHER PUBLICATIONS

Tsantrizos et al, "Macrocyclic Inhibitors of the NS3 Protease as Potential Therapeutic Agents of Hepatitis C Virus Infection," Angew. Chem. Int. Ed. (2003), vol. 42, pp. 1356-1360.*

(Continued)

*Primary Examiner* — Cecilia Tsang
*Assistant Examiner* — Thomas Heard
(74) *Attorney, Agent, or Firm* — Pamela A. Mingo

(57) ABSTRACT

Macrocyclic peptides having the general formula:

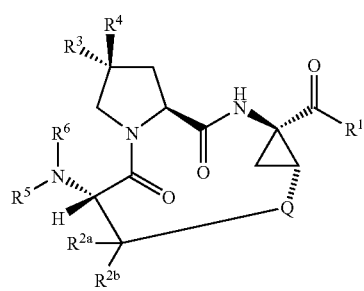

are disclosed. Compositions comprising the compounds and methods for using the compounds to inhibit HCV are also disclosed.

24 Claims, No Drawings

FOREIGN PATENT DOCUMENTS

| | | |
|---|---|---|
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |

OTHER PUBLICATIONS

U.S. Appl. No. 11/923,918, filed Oct. 25, 2007, D'Andrea et al.
U.S. Appl. No. 11/923,948, filed Oct. 25, 2007, D'Andrea et al.
U.S. Appl. No. 11/923,977, filed Oct. 25, 2007, D'Andrea et al.
U.S. Appl. No. 11/934,840, filed Nov. 5, 2007, Sin et al.
U.S. Appl. No. 11/939,768, filed Nov. 14, 2007, Wang et al.
U.S. Appl. No. 11/937,780, filed Nov 14, 2007, Wang et al.
Lauer G. M. et al., "Hepatitis C Virus Infection," New England Journal of Medicine, vol. 345 No. 1, pp. 41-52, (2001).
Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).
Llinas-Brunet et al. (2004) Journal of Medicinal Chemistry, vol. 47 pp. 6584-6594.

\* cited by examiner

HEPATITIS C VIRUS INHIBITORS

CROSS-REFERENCE TO RELATED APPLICATIONS

This application claims the benefit of U.S. Provisional Application Ser. No. 60/866,120 filed Nov. 16, 2006.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In a first aspect the present disclosure provides a compound of formula (I)

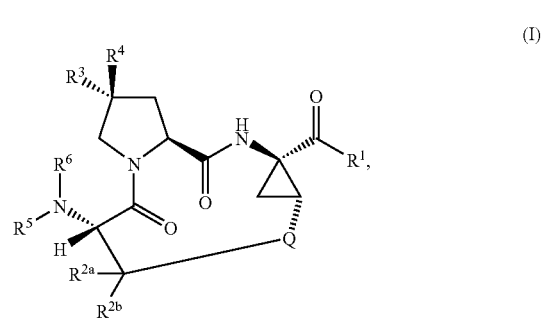

or a pharmaceutically acceptable salt thereof, wherein $R^1$ is selected from alkoxy, hydroxy, and —NHSO$_2$R$^7$;

$R^{2a}$ and $R^{2b}$ are independently selected from hydrogen and methyl;

$R^3$ is selected from alkenyl, alkyl, aryl, arylalkyl, cycloalkyl, (cycloalkyl)alkyl, heterocyclyl, and heterocyclylalkyl; provided that when $R^4$ is hydrogen then $R^3$ is other than heterocyclyl;

$R^4$ is selected from hydrogen and hydroxy;

$R^5$ is selected from hydrogen, alkyl, and cycloalkyl;

$R^6$ is selected from hydrogen, alkyl, alkoxycarbonyl, alkylaminocarbonyl, alkylcarbonyl, aminocarbonyl, aryloxycarbonyl, cycloalkyloxycarbonyl, dialkylaminocarbonyl, haloalkoxycarbonyl, haloalkyl, haloalkylcarbonyl, heterocyclyloxycarbonyl, and (NR$^a$R$^b$)sulfonyl;

$R^7$ is selected from alkyl, aryl, cycloalkyl, (cycloalkyl)alkyl, heterocyclyl, and —NR$^a$R$^b$; wherein the cycloalkyl and the cycloalkyl part of the (cycloalkyl)alkyl are optionally substituted with one, two, or three groups independently selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and (NR$^e$R$^f$)carbonyl; and wherein R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl; and wherein R$^e$ and R$^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo; and Q is a C$_{3-9}$ saturated or unsaturated chain, optionally containing one to three heteroatoms independently selected from O, S(O)$_m$, and NR$^9$, wherein m is 0, 1, or 2, and R$^9$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkyloxy, dialkylaminocarbonyl, dialkylaminocarbonylalkyl, haloalkyl, and heterocyclylcarbonyl.

In a first embodiment of the first aspect the present disclosure provides a compound of formula (I), or a pharmaceutically acceptable salt thereof, wherein $R^4$ is hydroxy.

In a second embodiment of the first aspect the present disclosure provides a compound of formula (I), or a pharmaceutically acceptable salt thereof, wherein $R^1$ is —NHSO$_2$R$^7$. In a third embodiment of the first aspect $R^7$ is cycloalkyl.

In a fourth embodiment of the first aspect the present disclosure provides a compound of formula (I), or a pharmaceutically acceptable salt thereof, wherein $R^{2a}$ and $R^{2b}$ are hydrogen.

In a fifth embodiment of the first aspect the present disclosure provides a compound of formula (I), or a pharmaceutically acceptable salt thereof, wherein Q is a $C_{5-7}$ unsaturated chain containing zero heteroatoms. In a sixth embodiment of the first aspect Q is a $C_6$ unsaturated chain containing zero heteroatoms.

In a second aspect the present disclosure provides a compound of formula (II)

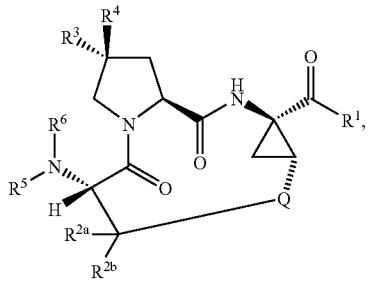

(II)

or a pharmaceutically acceptable salt thereof, wherein
$R^1$ is —NHSO$_2$R$^7$;
$R^{2a}$ and $R^{2b}$ are hydrogen;
$R^3$ is selected from alkenyl, alkyl, aryl, arylalkyl, cycloalkyl, (cycloalkyl)alkyl, heterocyclyl, and heterocyclylalkyl; provided that when $R^4$ is hydrogen then $R^3$ is other than heterocyclyl;
$R^4$ is selected from hydrogen and hydroxy;
$R^5$ is hydrogen;
$R^6$ is alkoxycarbonyl;
$R^7$ is selected from alkyl, aryl, cycloalkyl, (cycloalkyl)alkyl, heterocyclyl, and —NR$^a$R$^b$; wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl; and Q is a $C_{3-9}$ saturated or unsaturated chain, optionally containing one to three heteroatoms independently selected from O, S(O)$_m$, and NR$^9$, wherein m is 0, 1, or 2, and $R^9$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkyloxy, dialkylaminocarbonyl, dialkylaminocarbonylalkyl, haloalkyl, and heterocyclylcarbonyl.

In a first embodiment of the second aspect the present disclosure provides a compound of formula (II), or a pharmaceutically acceptable salt thereof, wherein $R^4$ is hydroxy.

In a second embodiment of the second aspect the present disclosure provides a compound of formula (II), or a pharmaceutically acceptable salt thereof, wherein $R^7$ is cycloalkyl.

In a third embodiment of the second aspect the present disclosure provides a compound of formula (II), or a pharmaceutically acceptable salt thereof, wherein Q is a $C_6$ unsaturated chain containing zero heteroatoms.

In a third aspect the present disclosure provides a compound selected from

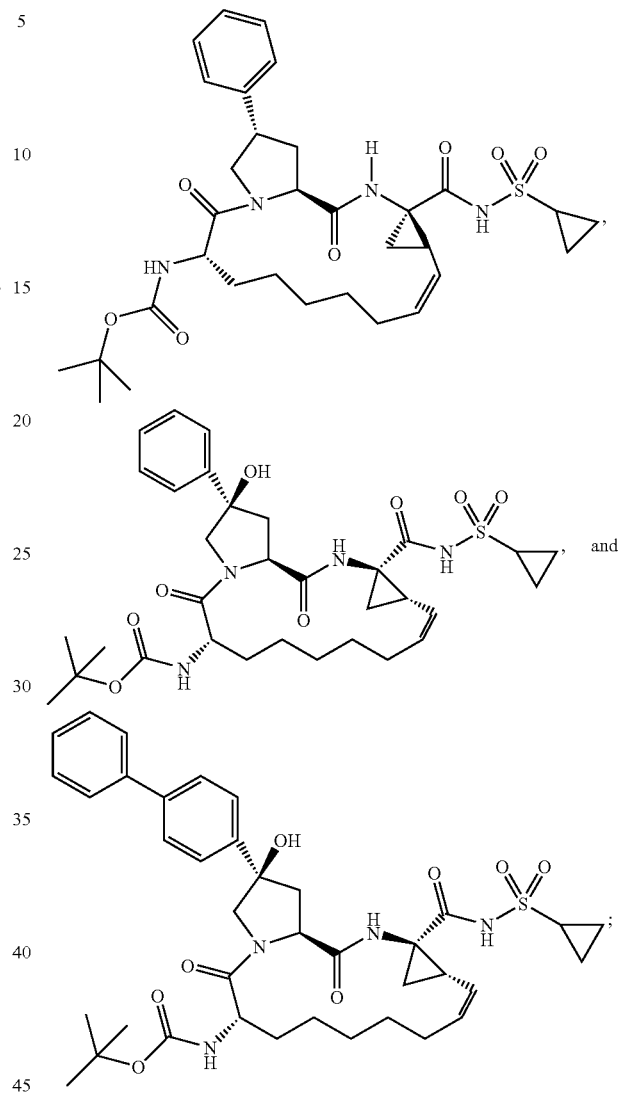

or a pharmaceutically acceptable salt thereof.

In a fourth aspect the present disclosure provides a composition comprising a compound of formula (I), or a pharmaceutically acceptable salt thereof, and a pharmaceutically acceptable carrier. In a first embodiment of the fourth aspect the composition further comprises at least one additional compound having anti-HCV activity. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastiod interferon tau.

In a fourth embodiment of the fourth aspect the present disclosure provides a composition comprising a compound of formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fourth aspect the present disclosure provides a composition comprising a compound of formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fifth aspect the present disclosure provides a method of treating an HCV infection in a patient, comprising administering to the patient a therapeutically effective amount of a compound of formula (I), or a pharmaceutically acceptable salt thereof. In a first embodiment of the fifth aspect the method further comprises administering at least one additional compound having anti-HCV activity prior to, after, or simultaneously with the compound of formula (I), or a pharmaceutically acceptable salt thereof. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau.

In a fourth embodiment of the fifth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fifth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a sixth aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of the sixth aspect the composition comprises three or four additional compounds having anti-HCV activity. In a second embodiment of the sixth aspect the composition comprises one or two additional compounds having anti-HCV activity.

In a seventh aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the seventh aspect the method comprises administering three or four additional compounds having anti-HCV activity. In a second embodiment of the seventh aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substitutent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "amino," as used herein, refers to —NH$_2$.

The term "aminocarbonyl," as used herein, refers to an amino group attached to the parent molecular moiety through a carbonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkenyl, alkoxy, alkoxycarbonyl, alkyl, a second aryl group, arylalkyl, aryloxy, cyano, cyanoalkyl, halo, haloalkoxy, haloalkyl, heterocyclyl, heterocyclylalkyl, nitro, and oxo; wherein the second aryl group, the aryl part of the arylalkyl and the aryloxy, the heterocyclyl, and the heterocyclyl part of the heterocyclylalkyl can be further optionally substituted with one, two, three, four, or five substituents independently selected from alkenyl, alkoxy, alkyl, cyano, halo, haloalkoxy, haloalkyl, nitro, and oxo.

The term "arylalkyl," as used herein, refers to an alkyl group substituted with one, two, or three aryl groups.

The term "arylcarbonyl," as used herein, refers to an aryl group attached to the parent molecular moeity through a carbonyl group.

The term "aryloxy," as used herein, refers to an aryl group attached to the parent molecular moeity through an oxygen atom.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "cyano," as used herein, refers to —CN.

The term "cyanoalkyl," as used herein, refers to an alkyl group substituted with one, two, or three cyano groups.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "(cycloalkyl)alkyl," as used herein, refers to an alkyl group substituted with one, two, or three cycloalkyl groups.

The term "dialkylamino," as used herein, refers to —NR$_2$, wherein each R group is an alkyl group. The two R groups may be the same or different.

The term "dialkylaminocarbonyl," as used herein, refers to a dialkylamino group attached to the parent molecular moiety through a carbonyl group.

The term "dialkylaminocarbonylalkyl," as used herein, refers to an alkyl group substituted with one, two, or three dialkylaminocarbonyl groups.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "haloalkylcarbonyl," as used herein, refers to a haloalkyl group attached to the parent molecular moiety through a carbonyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four to seven-membered, preferably four- to six-membered, aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkenyl, alkoxy, alkoxycarbonyl, alkyl, aryl, arylalkyl, aryloxy, cyano, cyanoalkyl, halo, haloalkoxy, haloalkyl, a second heterocyclyl group, heterocyclylalkyl, nitro, and oxo; wherein the aryl, the aryl part of the arylalkyl and the aryloxy, the second heterocyclyl, and the heterocyclyl part of the heterocyclylalkyl can be further optionally substituted with one, two, three, four, or five substituents independently selected from alkenyl, alkoxy, alkyl, cyano, halo, haloalkoxy, haloalkyl, nitro, and oxo.

The term "heterocyclylalkyl," as used herein, refers to an alkyl group substituted with one, two, or three heterocyclyl groups.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom. R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl.

The term "(NR$^a$R$^b$)sulfonyl," as used herein, refers to an —NR$^a$R$^b$ group attached to the parent molecular moiety through a sulfonyl group.

The term "—NR$^e$R$^f$," as used herein, refers to two groups, R$^e$ and R$^f$ which are attached to the parent molecular moiety through a nitrogen atom. R$^e$ and R$^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "(NR$^e$R$^f$)carbonyl," as used herein, refers to an —NR$^e$R$^f$ group attached to the parent molecular moiety through a carbonyl group.

The term "oxo," as used herein, refers to =O.

The term "sulfonyl," as used herein, refers to SO$_2$.

The compounds of the present disclosure can exist as prodrugs. The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

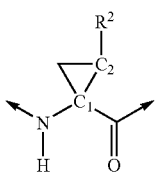

P1 wherein $C_1$ and $C_2$ each represent an asymmetric carbon atom at positions 1 and 2 of the cyclopropyl ring.

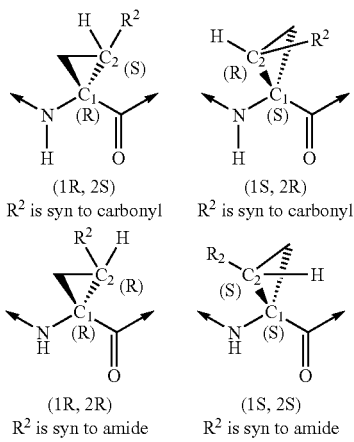

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Pharmaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim |

TABLE 1-continued

| Brand Name | Physiological Class | Type of Inhibitor or Target | Source Company |
|---|---|---|---|
| | | | Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | Glaxo SmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |

TABLE 1-continued

| Brand Name | Physiological Class | Type of Inhibitor or Target | Source Company |
|---|---|---|---|
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| TMC-465350 | Antiviral | serine protease inhibitor | Medivir/Tibotec |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

Chemical abbreviations commonly used to identify chemical compounds disclosed herein include Bn: benzyl; Boc: tert-butyloxycarbonyl {Me$_3$COC(O)}; BSA: bovine serum albumin; CDI: carbonyldiimidazole; DBU: 1,8-diazabicyclo [5.4.0]-undec-7-ene; CH$_2$Cl$_2$=DCM: methylene chloride; TBME: tert-butyl methyl ether; DEAD: diethylazodicarboxylate; DIAD: diisopropylazodicarboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; Et: ethyl; EtOH: ethanol; EtOAc: ethyl acetate; Et$_2$O: diethyl ether; Grubb's Catalyst: bis(tricyclohexylphosphine)benzylidene ruthenium (IV) dichloride; Grubb's 2$^{nd}$ Generation Catalyst: tricyclohexylphosphine[1,3-bis(2,4,6-trimethylphenyl)-4,5-dihydroimidazol-2-ylidene][benzylidene]ruthenium (IV) dichloride; HATU: [O-(7-azabenzotriazol-1-yl)-N,N,N',N'-tetramethyluronium hexafluorophosphate; HBTU: [O-(1H-benzotriazol-1-yl)-N,N,N',N'-tetramethyluronium hexafluorophosphate; HOBT, 1-hydroxybenzotriazole; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrolidine; Pr: propyl; PPA: polyphosphoric acid; TBAF: tetra-n-butylammonium fluoride; 1,2-DCE or DCE: 1,2-dichloroethane; TFA: trifluoroacetic acid; THF: tetrahydrofuran.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

As shown in Scheme 1, intermediates of the present disclosure such as dipeptide (1), can be used for the preparation of compounds of formula (I). In the first step of this process the Boc protected nitrogen of (1) is deprotected using an acid such as HCl in a solvent such as ether, to provide the corresponding free amine 2. Amine (2) can be subsequently coupled to amino acid (3) using a coupling agent such as HATU in a solvent such as dichloromethane to provide the tripeptide intermediate (4). It should be noted that in some cases intermediates like (3) are commercially available, and alternatively such compounds can be readily prepared in racemic or chiral fashion by methods known in the art. A key transformation in the construction of compounds of formula (I) is the macrocyclization process wherein intermediates of general structure (4) are converted into intermediates of general structure (5). In the general example cited, the conversion of intermediate (4) into (5) can be affected by an intramolecular olefin metathesis reaction. This class of reactions is well established in the art and as such, a number of olefin-metathesis-catalysts have been developed and are commercially available. For example the conversion of diene (4) to macrocycle (5) could be affected by the treatment of (4) with a sufficient quantity of Grubb's first-generation olefin metathesis catalyst, in a solvent such as dichloromethane or dichloroethane. In some examples for the conversion of (4) to (5), it may be necessary to heat the reaction mixture in order to effect this cyclization process. Intermediate (5) is then converted to compounds of formula (I) such as (7) by a two step process. In the first step of this process, the ester functionality of intermediate (5) is hydrolyzed to the corresponding carboxylic acid (6). This transformation can be accomplished by a saponification reaction wherein (5) is treated with a base such as lithium hydroxide in a mixture of THF, methanol and water. The resulting acid (6) can be converted to a compound of formula (I) by a simple coupling reaction with a sulfonamide derivative as shown. For example, it is well established in the art that treatment of a carboxylic acid like (6), with CDI in a solvent such as methylene chloride, generates in situ a reactive intermediate which when treated with a sulfonamide provides for (7), a compound of formula (I).

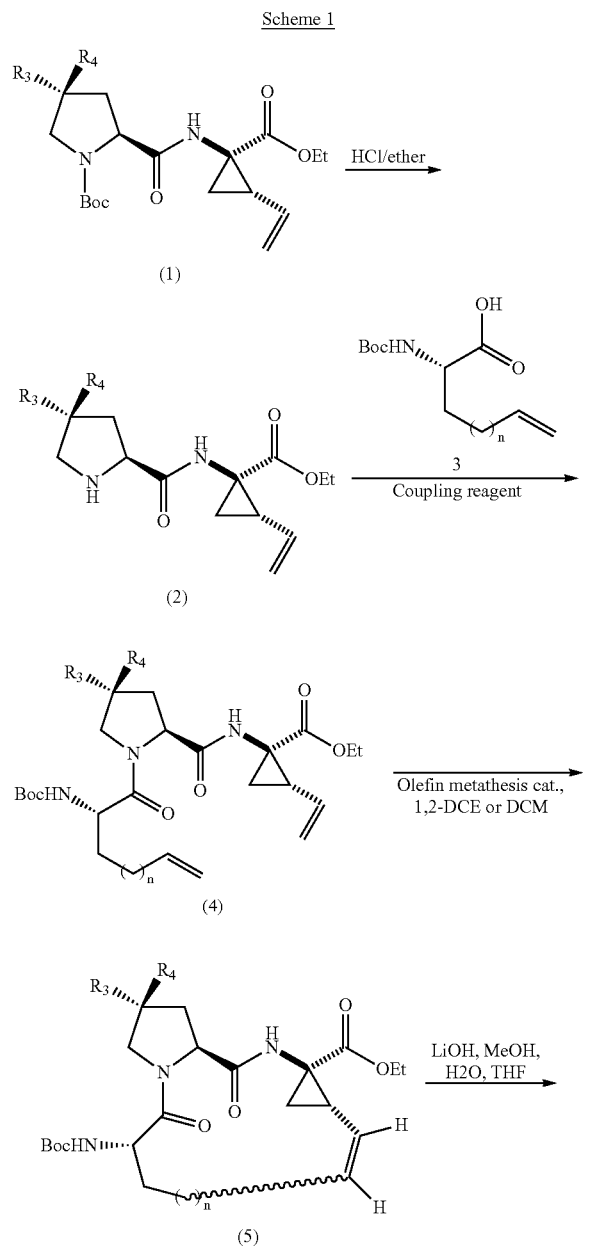

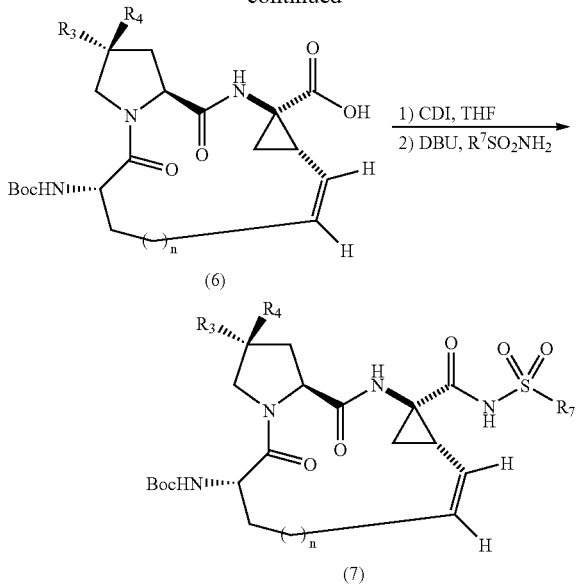

If, in the above final coupling process, that is in the conversion of (6) to (7), the $R^7SO_2NH_2$ entity is a sulfamide derivative, as for example $R^aR^bNSO_2NH_2$, then an alternative coupling procedure can be used. Therein the sulfamide intermediate (1) (Scheme 2) is first deprotonated using a base such as lithium bishexamethyldisilane in a solvent such as THF. The resulting THF solution of sulfamide anion (2) is then added to the aforementioned reaction mixture containing the activated carboxylic acid. This reaction mixture is then stirred for several hours to provide the requisite acylsulfamide (7).

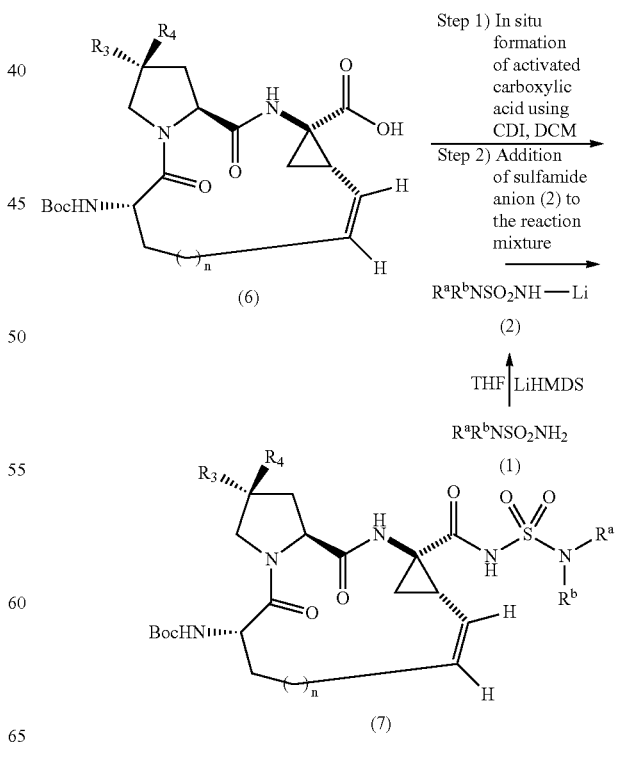

Compounds of formula (I) can also be converted into other compounds of formula I as described herein. An example of such a process is shown in Scheme 3, wherein a compound of formula I (1) which bears a Boc group at the P4 position is converted into a compound of formula I (3) wherein said compound bears a urea group at the P4 position. The conversion of (1) to (3) can be carried out in a two step process the first of which is the conversion of (1) to amine (2) by treatment of (1) with an acid such as TFA in a solvent such as methylene chloride. The resulting amine TFA salt can be treated with an isocyanate in the presence of one equivalent of base to provide a compound of formula I (3) wherein the P3 moiety is capped with a urea. As previously noted one skilled in the art will recognize that intermediate (2) can be used as starting material for the preparation of compounds of formula (I) wherein the P3 group is capped with an amide or a carbamate. The construction of said compounds of formula (I) can be achieved using standard conditions for the formation of said P4 functionalities from amines.

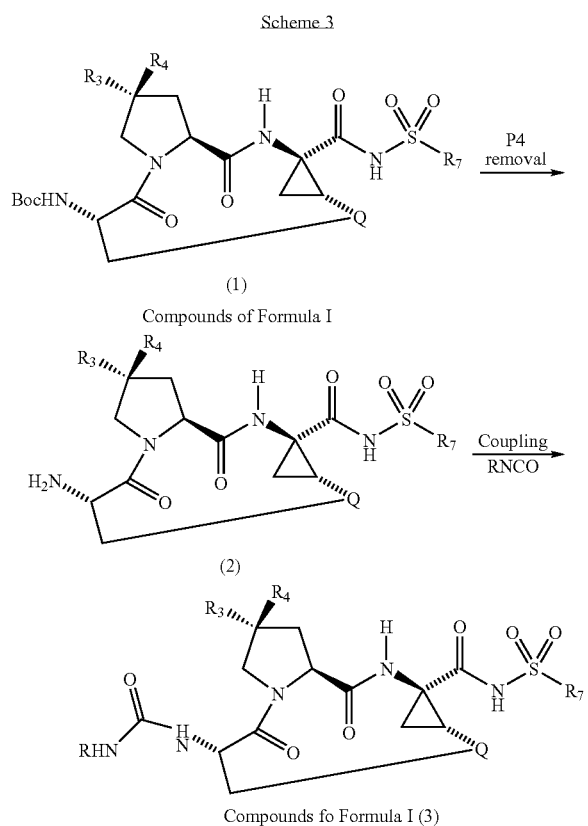

Non-limiting procedures for making P2 intermediates and compounds of formula (I) are shown in the Schemes below. Said intermediates, reaction conditions and methods given in the specific examples are broadly applicable to compounds with other substitution patterns. For example, the synthesis the P2 elements found in compounds of formula (I) of Scheme 4 can be prepared following the defined synthetic path. Therein commercially available N-Boc-4-oxo-L-proline is treated with an organometallic agent such as a Grignard reagent (or alternatively an alkyl or aryl lithium species, or alternatively an alkyl, or aryl zinc species) to provide intermediate (2) in which the C4 position of the proline bears an $R^3$ substituent and a free tertiary hydroxy group. Intermediate (2) can then be converted into compounds of formula (I).

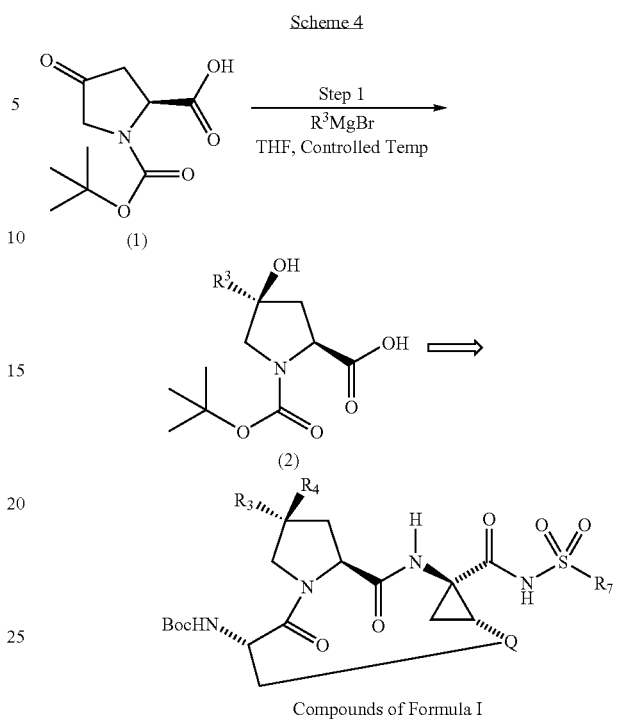

Compounds of formula (I) where $R^4$ is a hydrogen can be synthesized from the corresponding compound of formula (I) where $R^4$ is a hydroxy group. Alternatively, a compound of formula (I) wherein $R^4$ is a hydrogen can be synthesized from any of the intermediates used for the preparation of compounds of formula (I) wherein $R^4$ is a hydroxy group. For example compounds of formula (I) wherein $R^4$ is a hydrogen can be prepared as shown in Scheme 5. Said compounds (3) can be prepared from the corresponding hydroxy analogues (1). The process for the formation of compounds like (3) from compounds like (1) requires a reduction, or deoxygenation of the proline C4 hydroxy group. There is considerable art established for the reduction and or deoxygenation of alcohols and particularly tertiary alcohols that could provide for the formation of compounds like (3) from compounds like (1). For example the direct reduction of alcohols to the corresponding alkane (Process 1 of Scheme 5) has been reported in the following reference: *J. Org. Chem.* 2001, 66, 7741. Therein the reduction of alcohols to alkanes is described wherein said alcohol is treated with chlorodiphenylsilane and a catalytic amount of indium trichloride in a solvent such as dichloroethane to provide the corresponding alkane. Said reaction can be conducted at room temperature, but in some cases heating may be required. An alternative process for the formation of compounds of formula (I), wherein $R^4$ is a hydrogen, from compounds of formula (I) wherein $R^4$ is a hydroxy group, is shown as Process 2 in Scheme 5. Therein compounds like (1) are first converted to activated alcohols (2) and these intermediates are reduced to the corresponding alkane (for example using a Barton deoxygenation process). Alternatively, activated alcohols as shown in (2) can be reduced to the corresponding alkanes as for example using reducing agents. These processes for the conversion of (1) to (3) in Scheme 5 are well known to those skilled in the art.

Scheme 5

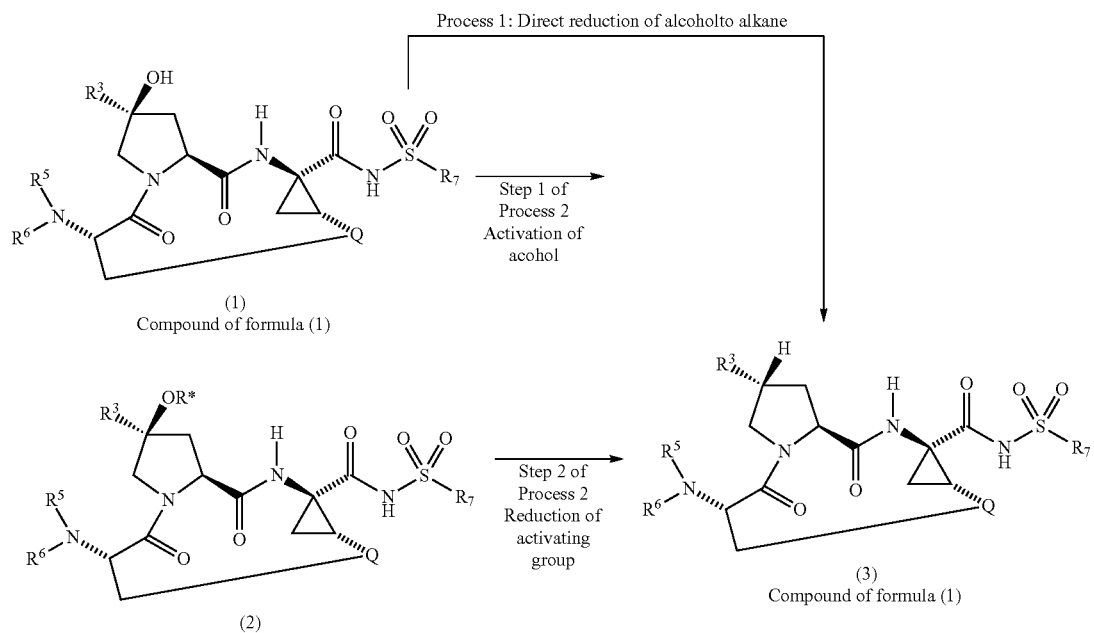

It should be noted that the addition of organometallic agents to the ketone moiety of proline derivative 1 (Scheme 6) is well established in the art. For example, Hruby and coworkers (*J. Org. Chem.* 2001, 66, 3593) have described the addition of phenylmagnesium bromide to intermediates of general structure (1) of Scheme 6. These findings provide evidence that optimal yields of the desired 1,2 addition products ((2), of Scheme 6) are obtained when a tert-butyl ester group is employed as a protecting group of the C2 carboxyl moiety. In addition, this work provided clear evidence in the form of X-ray crystallography as to the stereochemical outcome of this addition reaction. Specifically, as a result of the aforementioned Grignard addition to ketone (1), a single product was obtained wherein the C4 hydroxyl group and the C2 carboxyl group assume a syn relative orientation about the five membered ring. From this structure determination the face selectivity in the addition of $R^3M$ to the ketone of (1) was deduced to be alpha in the context of structure (1) of Scheme 6. That is, the organometallic selectively adds to the re-face (bottom face) of the carbonyl in (1) to provide the corresponding tertiary alcohol (2) with the stereochemistry shown.

Scheme 6

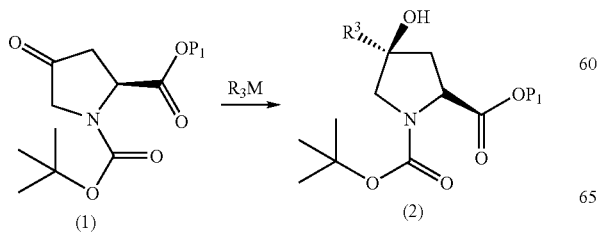

-continued

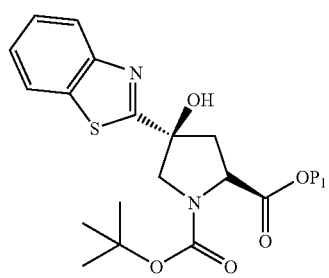
(2a)

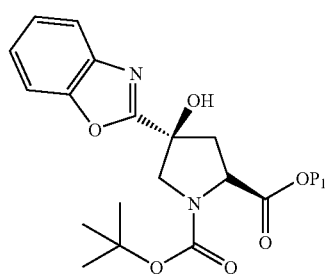
(2b)

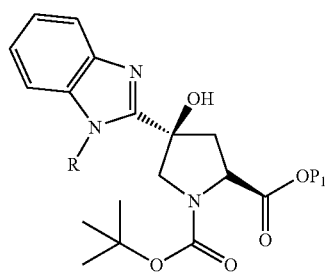
(2c)

-continued (2d) 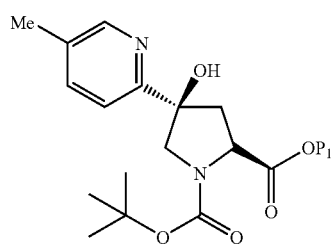

(2e) 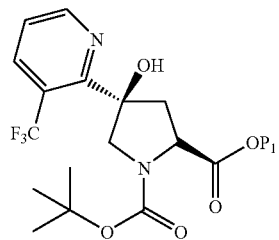

(2f) 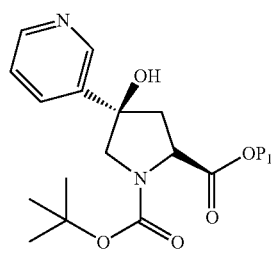

(2g) 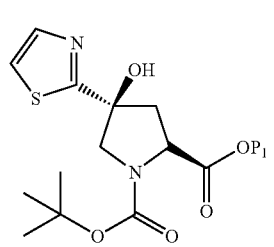

(2h) 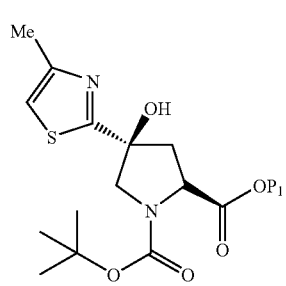

(2i) 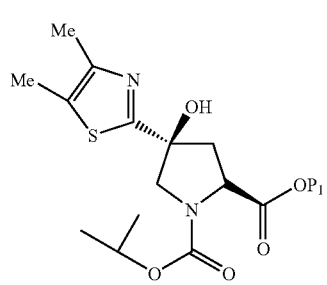

-continued (2j) 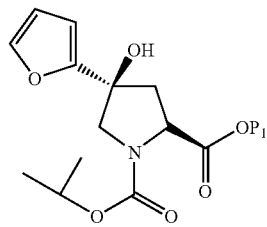

(2k) 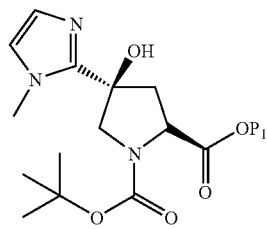

(2l) 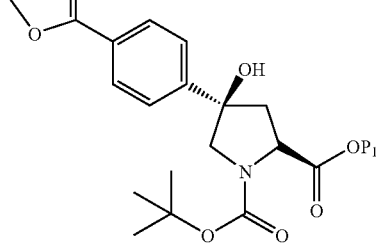

(2m) 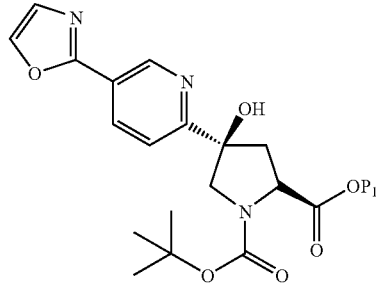

The aforementioned work of Hruby describes the addition of a specific Grignard reagent to derivatives of (1) (Scheme 6). However, the addition of a variety of Grignard reagents to proline (1) is encompassed in the present disclosure. The body of literature that describes the addition of organometallic agents, including Grignard reagents, to ketones is considerable and is summarized in general overviews in the art such as: *Comprehensive Organic Functional Group Transformations*. Volume 2: *Synthesis: Carbon with one heteroatom attached by a single bond*. Editor in Chief Alan. R. Katritzky, et al. 1995. Chapter 2.02, page 37. This class of reactions is also described in *Comprehensive Organic Synthesis*. Editor in Chief Barry M Trost, Volume 1: Additions to C—X pi-bonds (part 1). 1991.

Recent research in the art provides conditions for further optimization of Grignard reagents in addition reactions to ketones and these works may be useful in the present disclosure. For example, Ishihara and co-workers (*Org. Lett.* 2005, Vol. 7, No. 4, 573) recently described the formation and utility of magnesium ate complexes. Magnesium ate comples, $R^3MgLi$, are derived from Grignard reagents and alkyllithiums. As described by Ishihara these complexes provide excellent yields of 1,2 addition products in reactions to ketones. In a separate study, Knochel and co-workers (*Angew. Chem. Int. Ed.* 2006, 45, 497) have described the use of soluble Lanthanide salts such as LnCl$_3$ in conjunction with organomagnesium reagents. The presence of these Lanthanide salts results in an improvement in the efficiency of the 1,2 addition reaction to carbonyl compounds. These works, and references cited therein, establish the state of the art with respect to the optimization of the Grignard reaction in simple additions to carbonyl compounds and serve as an important source of information in the present disclosure.

It should also be noted that a range of organometallic reagents participate in addition reactions to ketones. Included in this body of work are reagents such as aryllithium, alkyllithium and heteroaryllithium reagents, which are well known to add in a 1,2 fashion to carbonyl moieties. For example, in a recent study by Dondoni and co-workers (*J. Org. Chem.* 2005, 70, 9257) benzothioazole is lithiated using BuLi and the resulting C2-lithium species adds in a 1,2 fashion to a lactone. By way of analogy lithiated benzothiazole would be expected to add in a 1,2 fashion to ketone (1) of Scheme 6 to provide an intermediate like (2a).

One skilled in the art would recognize that organometallic reagents derived from heterocycles such as oxazoles and thiazoles and imidazoles can also participate in 1,2 addition reactions to ketone (1). There is a considerable body of literature that defines the unique conditions employed for each of these heterocycle systems and this information is readily available to one skilled in the art. For example, the use of organometallic reagents derived from benzoxazole or oxazole, in addition reactions to ketones requires the use of lithium magnesates. The specifics of this recent study by Bayh and co-workers is described in *J. Org. Chem.*, 2005, 70, 5190. The addition of benzoxazole to ketone (1) of Scheme 6 would provide access to intermediates like (2b).

There is significant literature precedent for the addition to ketones using a wide range of organometallic reagents derived from heterocycles. For example the work of Behinda and co-workers (Tet. Lett. 42, 2001, 647) describes the formation of a lithiated benzimidazole and its addition to a simple lactone. By analogy, the use of this lithiated benzimidazole in addition reactions to ketone (1) of Scheme 6 would provide access to intermediates like (2c). In addition, a recent study by Kawasaki and co-workers (*Bioorganic and Medicinal Chem. Lett.* 13, 2003, 87) describes the formation of a series of lithiated heteroaromatic compounds and their addition reactions to activated amides. By analogy the use of these lithiated heteroaromatic intermediates in addition reactions to ketone (1) of Scheme 6 would provide access to intermediates (2d-2k).

The employment of organometallics derived from biaryl, or heteroaryl-aryl systems in addition 1,2 reactions to ketone (1) is also pertinent to the present disclosure. The addition of this class of organometallic reagents to ketone (1) would provide access to intermediates like (2l) and (2m). It should be noted that in the exemplification of the present disclosure, it may be necessary to synthesize biaryl, or hetero-aryl organometallics for subsequent use in addition reactions to ketone (1) of Scheme 6. One skilled in the art would recognize the significant body of literature which describes the preparation of organometallics of this type and precursors thereof. For example a recent review by Chinchilla and co-workers (*Chem. Rev.* 2004, 104, 2667) describes the preparation of metalated heterocycles and their utility. The basic chemistry for the preparation of biaryl or heteroaryl-aryl systems often employ Suzuki like coupling reactions. A body of literature put forth by Gregory Fu describes the state of the art in such coupling reactions and a subset of these references follow: *JACS* 2004, 126, 1340; *JACS*, 2002, 124, 13662; *Angew. Chem. Int. Ed.* 2002, 41, No. 11, 1945; *Angew. Chem. Int. Ed.* 2002, 41, No. 20, 3910; *JACS* 2002, 122, 4020; *JACS* 2001, 123, 10099; *Org. Lett.* 2001, Vol. 3, No. 26, 4295; *Angew. Chem. Int. Ed.* 1998, 37, No. 24, 3387. In addition to this body of work critical reviews in the area are readily available such as by Rossi in *Synthesis* 2004, No. 15, 2419.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel (SiO$_2$) according to Still's flash chromatography technique (*J. Org. Chem.* 1978, 43, 2923).

Example 1

Preparation of Sulfamides

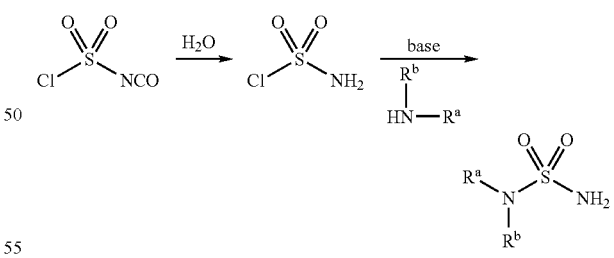

The intermediate sulfamoyl chloride was prepared by addition of water (1 equiv) in THF to a cold (−20° C.) stirred solution of chlorosulfonyl isocyanate (1 equiv) in THF and the resulting solution allowed to warm to 0° C. To this solution was added anhydrous Et$_3$N (1 equiv) followed by requisite secondary amine (1 equiv). The reaction mixture was warmed to room temperature, then filtered and the filtrate was rotary evaporated to afford the desired sulfamides. Said sulfamide was then coupled to a carboxylic acid to provide the desired acylsulfamide.

Example 2

Specific Procedure for the Preparation of an Acylsulfamide Intermediate

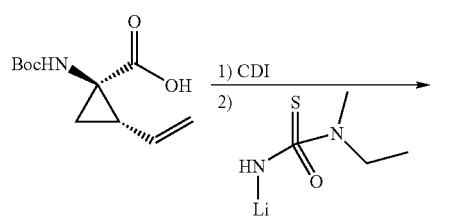

↓ Base

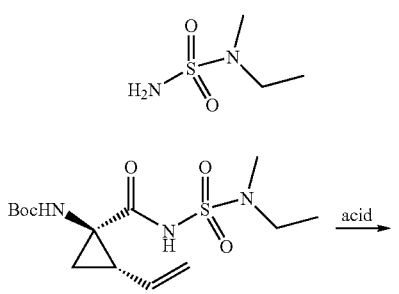

↓

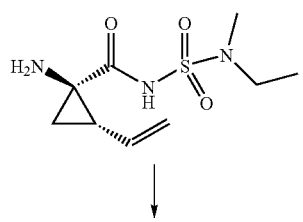

↓

Compounds of Formula I

To a solution of (1R,2S)1-tert-butoxycarbonylamino-2-vinylcyclopropanecarboxylic acid (217 mg, 1.194 mmol) in THF (5 mL), CDI (290 mg, 1.791 mmol) was added and the reaction mixture was heated under reflux for 45 min. In another round-bottomed flask, LiHMDS (1.0 M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. Two reaction mixtures were added together and stirred at room temperature for 2 h. Water was added to quench the reaction and the reaction solution was extracted with EtOAc. The organic layer was separated and dried over MgSO$_4$. Evaporation of solvent gave crude product which was purified by Prep. HPLC to afford desired N-acylsulfamide. N-acylsulfamide was then dissolved in 4N HCl solution in dioxane (2 mL) and stirred at rt for 4 h. Evaporation of solution give brownish oil as HCl salt. (112 mg, 33% yield). $^1$H NMR (400 Mz, CD$_3$OD) δ1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 min.), MS m/z 270 (M+Na$^+$).

Example 3

Preparation of racemic (1R,2S)/(1S,2R)-1-amino-2-vinylcyclopropane carboxylic acid ethyl ester hydrochloride (Method A and Method B)

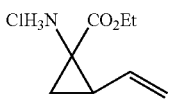

The named compound was made racemic by each of the following methods A and B.

Method A

Preparation of N-Benzyl Imine of Glycine Ethyl Ester

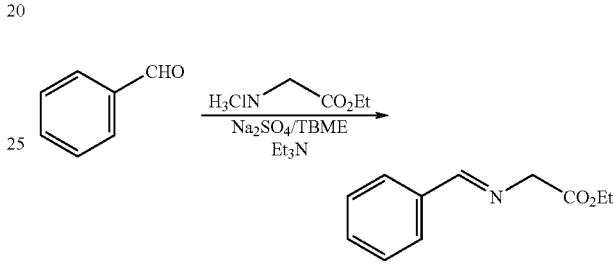

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO$_3$ (1 L) and brine (1 L). The solution was dried over MgSO$_4$, concentrated in vacuo to afford 392.4 g of the N-benzyl imine product as a thick yellow oil that was used directly in the next step. $^1$H NMR (CDCl$_3$, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Preparation of racemic N-Boc-(1R,2S)/(1S,2R)-1-amino-2-vinylcyclopropane carboxylic acid ethyl ester

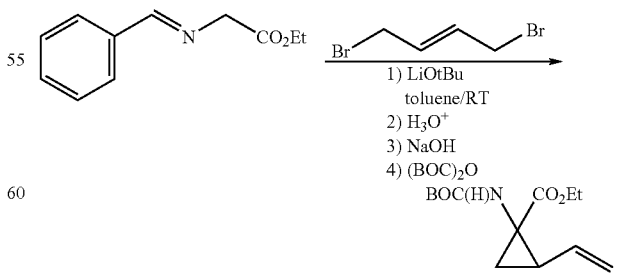

To a suspension of lithium tert-butoxide (84.06 g, 1.05 mol) in dry toluene (1.2 L), was added dropwise a mixture of the N-benzyl imine of glycine ethyl ester (100.4 g, 0.526 mol)

and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1 L. To this solution of free amine, was added BOC$_2$O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

Preparation of Racemic
(1R,2S)/(1S,2R)1-amino-2-vinylcyclopropane
carboxylic acid ethyl ester hydrochloride

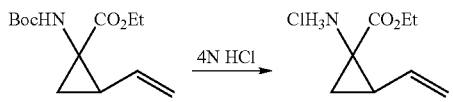

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quantitative yield (7 g, 100%). $^1$H NMR (methanol-d$_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2, 1H), 5.69-5.81 (m, 1H).

Method B

Preparation of Racemic
N-Boc-1-amino-2-vinylcyclopropane carboxylic acid
ethyl ester hydrochloride

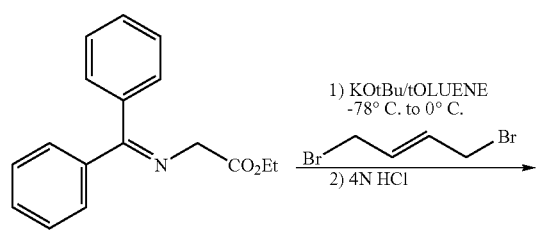

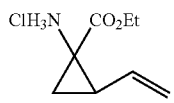

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Example 4

Resolution of
N-Boc-(1R,2S)/(1S,2R)-1-amino-2-vinylcyclopropane
carboxylic acid ethyl ester

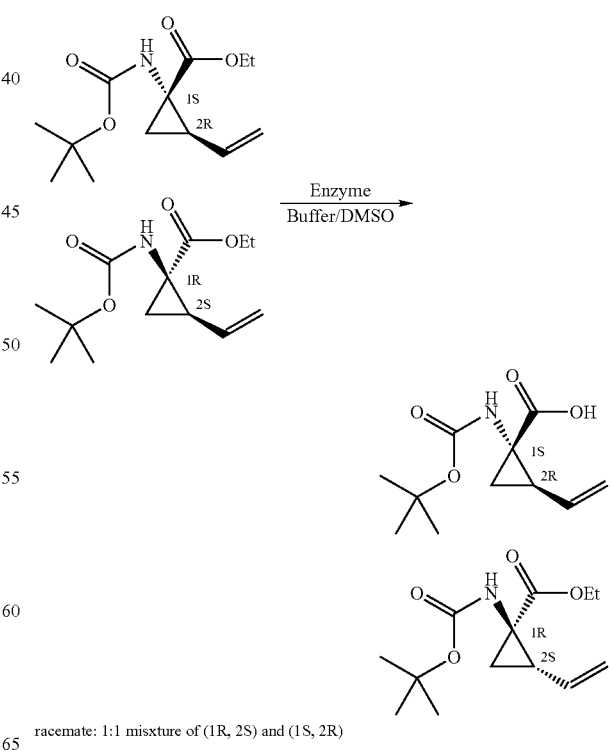

racemate: 1:1 misxture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nanomolar ("nM"), containing no acid; 100% enantiomeric excess ("ee").

The aqueous layer from the extraction process was then acidified to pH 2 with 50% H$_2$SO$_4$ and extracted with MTBE (2×2 L). The MTBE extract was washed with water (3×100 mL) and evaporated to give the acid as light yellow solid (42.74 g; purity: 99% @ 210 nM, containing no ester).

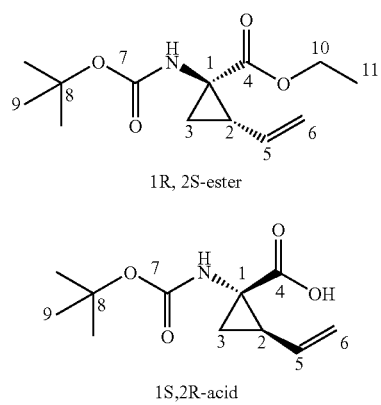

1R, 2S-ester 1S,2R-acid

| ester | acid |
|---|---|
| High Resolution Mass Spec | (+) ESI, C13H22NO4, [M + H]$^+$, cal. 256.1549, found 256.1542 | (−) ESI, C11H16NO4, [M − H]$^-$, cal. 226.1079, found 226.1089 |

NMR observed chemical shift
Solvent: CDCl$_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

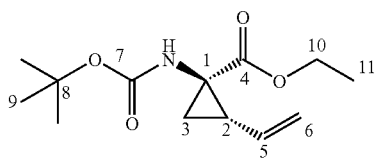

1R, 2S-ester

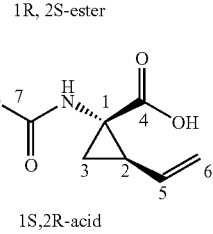

1S,2R-acid

Resolution B

To 0.5 mL 100 millimolar ("mM") Heps.Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("µl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Resolution C

To 0.5 ml 100 mM Heps.Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 µl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Samples analysis was carried out in the following manner:
1) Sample preparation: About 0.5 ml of the reaction mixture was mixed well with 10 volume of EtOH. After centrifugation, 10 μl of the supernatant was injected onto HPLC column.
2) Conversion determination:
Column: YMC ODS A, 4.6×50 millimeter ("mm"), S-5 μm
Solvent: A, 1 mM HCl in water; B, MeCN
Gradient: 30% B for 1 min; 30% to 45% B over 0.5 min; 45% B for 1.5 min; 45% to 30% B over 0.5 min.
Flow rate: 2 ml/min
UV Detection: 210 nM
Retention time: acid, 1.2 min; ester, 2.8 min.
3) Enantio-excess determination for the ester:
Column: CHIRACEL OD-RH, 4.6×150 mm, S-5 μm
Mobile phase: MeCN/50 mM $HClO_4$ in water (67/33)
Flow rate: 0.75 ml/min.
UV Detection: 210 nM.
Retention time:
(1S,2R)-1-amino-2-vinylcyclopropane carboxylic acid 5.2 min;
Racemate (1R,2S)/(1S,2R)-1-amino-2-vinylcyclopropane carboxylic acid ethyl ester 18.5 min and 20.0 min;
(1R,2S)-1-amino-2-vinylcyclopropane carboxylic acid ethyl ester 18.5 min.
Resolution D
5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hour and the reaction was slowly cooled down to room temperature (about 25° C.) and stirred overnight. pH of the reaction mixture was adjusted to 8.5 with 10 N NaOH and the mixture was extracted with MTBE (2×4 L). The combined MTBE extract was washed with 5% $NaHCO_3$ (3×400 ml) and water (3×400 ml), and evaporated to give enantiomerically pure N-Boc-(1R,2S)/-1-amino-2-vinylcyclopropane carboxylic acid ethyl ester as light yellow crystal (259 g; purity: 96.9% (210 nM, containing no acid; 100% ee).
Resolution E
10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.) was added to the reactor. When temperature of the mixture closed to 38° C., pH was adjusted to 8.0 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, pH was adjusted to 8.0 with 10 N NaOH. After 21 hours, the reaction was cooled down to 25° C. pH of the reaction mixture was adjusted to 8.5 with 10 N NaOH and the mixture was extracted with MTBE (2×5 L). The combined MTBE extract was washed with 5% $NaHCO_3$ (3×500 ml) and water (3×200 ml), and evaporated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% (210 nM, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of
N-Boc-(1R,2S)-1-amino-2-vinylcyclopropane
carboxylic acid ethyl ester

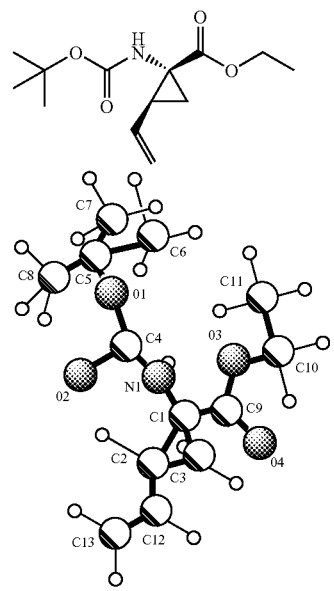

Structure of
N-Boc-(1R,2S)-1-amino-2-vinylcyclopropane
carboxylic acid ethyl ester

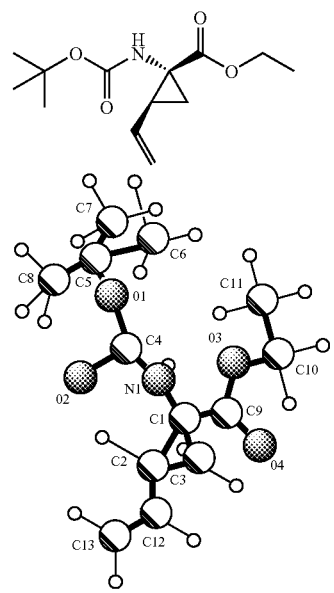

Crystal Data Experimental:
Chemical formula: C13H21N1O4 Crystallization
Crystal system: Orthorhombic Crystal source: MTBE
Space Group: P2$_1$2$_1$2$_1$ Crystal description: Colorless rod
a=5.2902(1) Å α=90 Crystal size (mm): 0.12×0.26×0.30
b=13.8946(2) Å β=90° Data Collection
c=19.9768(3) Å γ=90° Temperature (K): 293
V=1468.40(4) Å$^3$ θ$_{max}$(°): 65.2 (Cu Kα)
Z=4 d$_x$=1.155 g cm$^{-3}$ No. of reflections measured: 7518
No. of reflections for lattice parameters: 6817 No. of independent reflections: 2390 (R$_{int}$=0.0776)
θ range for lattice parameters (°): 2.2-65.2 No. of observed reflections (I≧2σ: 2284
Absorption coefficient (mm$^{-1}$): 0.700 Absorption correction (T$_{min}$-T$_{max}$): 0.688-1.000
Resolution F 5 L of 0.2 M sodium borate buffer (pH 9) was maintained at 45° C. in a 20 liter jacked reactor, stirred at 400 rpm. Three liter of DI water and four liters of Savinase 16 L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 min, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hour, temperature was lowered to 35° C. At 42 hour, temperature was raised to 48° C. and pH was adjusted to 9.0 with 10 N NaOH. Heating was stopped at 48 hour and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO$_3$ (6×300 ml) and water (3×300 ml), and evaporated to give enantiomerically pure N-Boc-(1R,2S)/-1-amino-2-vinylcyclopropane carboxylic acid ethyl ester as light yellow crystal (101A g; purity: 95.9% (210 nM, containing no acid; 98.6% ee).

Example 5

Step 1: Preparation of ethyl 1(R)-amino-2(S)-vinylcyclopropane carboxylate hydrochloride

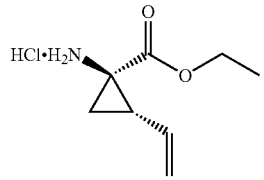

Ethyl 1(R)-tert-butoxycarbonylamino-2(S)-vinylcyclopropanecarboxylate (8.5 g, 33.3 mmol) was stirred under an N$_2$ atmosphere with 200 mL of 4N HCl/dioxane (Aldrich) at rt for 3 h. The solvent was removed under reduced pressure keeping the temperature below 40 C. This gave 6.57 g (~100%) of ethyl 1(R)-amino-2(S)-vinylcyclopropanecarboxylate hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

Step 2: Preparation of ethyl 1(R)-[1-tert-butoxycarbonyl-4(R)-hydroxypyrrolidine-2(S)-carboxamido]-2(S)-vinylcyclopropanecarboxylate

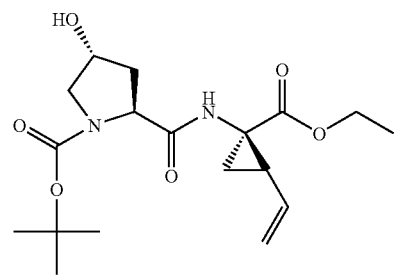

A stirred slurry of Boc-L-4-hydroxyproline (N-Boc (2S, 4R)-hydroxyproline) (10 g, 43.3 mmol) in 400 mL of methylene chloride was treated sequentially with N-methyl morpholine (9.3 mL, 84.7 mmol), HATU (19.5 g, 51.3 mmol), and ethyl 1(R)-amino-2(S)-vinylcyclopropanecarboxylate hydrochloride (9.1 g, 47.5 mmol). The gold homogeneous solution was stirred at rt under N$_2$ for 18 h, and then concentrated in vacuo to give a brown oil. This was partitioned between ethyl acetate and sat. aq. NaHCO$_3$. The organic phase was washed with brine, dried (MgSO$_4$), and concentrated in vacuo to give 15 g (94%) of ethyl 1(R)-[1-tert-butoxycarbonyl-4(R)-hydroxypyrrolidine-2(S)-carboxamido]-2(S)-vinylcyclopropanecarboxylate as a off-white solid: LC-MS (Xterra HPLC column: 3.0×50 mm length. Gradient: 100% Solvent A/0% Solvent B to 0% Solvent A/100% Solvent B. Gradient time: 3 min. Hold time: 1 min. Flow rate: 5 mL/min. Detector Wavelength: 220 nM. Solvent A: 10% MeOH/90% H$_2$O/0.1% TFA. Solvent B: 10% H$_2$O/90% MeOH/0.1% TFA.) (Retention time: 2.09 min), MS m/z 369 (M$^+$+1).

Step 3: Preparation of ethyl 1(R)-[4(R)-hydroxypyrrolidine-2(S)-carboxamido]-2(S)-vinylcyclopropanecarboxylate hydrochloride

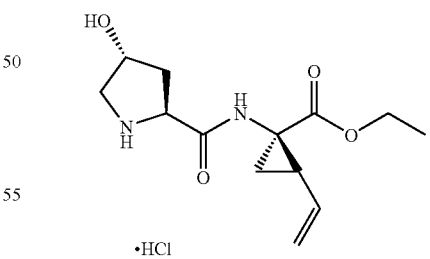

A stirred slurry of ethyl 1(R)-[1-tert-butoxycarbonyl-4(R)-hydroxypyrrolidine-2(S)-carboxamido]-2(S)-vinylcyclopropanecarboxylate (5.0 g, 13.6 mmol) was treated with 4N HCl/dioxane (20 mL) for 3 h. The reaction mixture was concentrated in vacuo to give 4.5 g (97%) of ethyl 1(R)-[4 (R)-hydroxypyrrolidine-2(S)-carboxamido]-2(S)-vinylcyclopropanecarboxylate hydrochloride as a white solid: $^1$H NMR (300 MHz, CD$_3$OD) δ 1.26 (t, J=7.14 Hz, 3H), 1.46 (dd, J=9.70, 5.31 Hz, 1H), 1.80 (dd, J=8.23, 5.31 Hz, 1H), 2.00-

2.15 (m, 1H), 2.18-2.30 (m, 1H), 2.45 (dd, J=13.36, 7.50 Hz, 1H), 3.36-3.48 (m, 1H), 4.11-4.24 (m, 2H), 4.44 (dd, J=10.25, 7.68 Hz, 1H), 4.58-4.65 (m, 1H), 4.84-4.94 (m, 1H), 5.17 (d, J=1.83 Hz, 1H), 5.27-5.42 (m, 1H), 5.67-5.89 (m, 1H).

Example 6

Preparation of Cyclopropylsulfonamide Methods A and B

Method A:

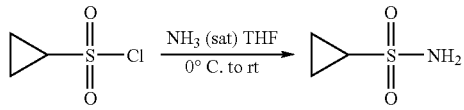

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1-2 mL of solvent remained, applied on to 30 g plug of SiO$_2$ (eluted with 30% to 60% EtOAc/Hexanes) to afford 3.45 g (100%) of cyclopropyl sulfonamide as a white solid. $^1$H NMR (Methanol-d$_4$) δ 0.94-1.07 (m, 4H), 2.52-2.60 (m, 1H); $^{13}$C NMR (methanol-d$_4$) δ 5.92, 33.01.

Method B:

Step 1: Preparation of N-tert-Butyl-(3-chloro)propylsulfonamide

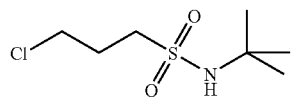

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in CH$_2$Cl$_2$ (2.0 L). The resulting solution was washed with 1 N HCl (1.0 L), water (1.0 L), brine (1.0 L) and dried over Na$_2$SO$_4$. It was filtered and concentrated in vacuo to give a slightly yellow solid, which was crystallized from hexane to afford the product as a white solid (316.0 g, 99%).

$^1$H NMR (CDCl$_3$) δ 1.38 (s, 9H), 2.30-2.27 (m, 2H), 3.22 (t, J=7.35 Hz, 2H), 3.68 (t, J=6.2 Hz, 2H), 4.35 (b, 1H).

Step 2: Preparation of Cyclopropanesulfonic acid tert-butylamide

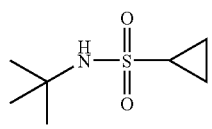

To a solution of N-tert-butyl-(3-chloro)propylsulfonamide (2.14 g, 10.0 mmol) in THF (100 mL) was added n-BuLi (2.5 M in hexane, 8.0 mL, 20.0 mmol) at −78° C. The reaction mixture was allowed to warm up to room temperature over period of 1 h. The volatiles were removed in vacuo. The residue was partitioned between EtOAC and water (200 mL, 200 mL). The separated organic phase was washed with brine, dried over Na$_2$SO$_4$, filtered and concentrated in vacuo. The residue was recrystallized from hexane to yield the desired product as a white solid (1.0 g, 56%). $^1$H NMR (CDCl$_3$) δ 0.98-1.00 (m, 2H), 1.18-1.19 (m, 2H), 1.39 (s, 9H), 2.48-2.51 (m, 1H), 4.19 (b, 1H).

Step 3: Preparation of cyclopropylsulfonamide

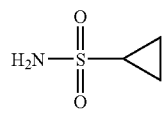

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).

$^1$H NMR (DMSO-d$_6$) δ 0.84-0.88 (m, 2H), 0.95-0.98 (m, 2H), 2.41-2.58 (m, 1H), 6.56 (b, 2H).

Example 7

Preparation of N-tert-butyl-(1-methyl)cyclopropylsulfonamide

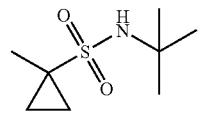

Step 1a Preparation of N-tert-butyl-(3-chloro)propylsulfonamide

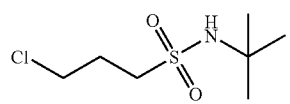

As shown above.

Step 1b. Preparation of N-tert-Butyl-(1-methyl)cyclopropylsulfonamide

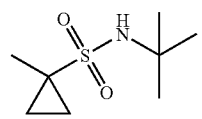

A solution of N-tert-butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to −78° C., and a solution of n-BuLi (20 mmol, 8 mL, 2.5 M in hexane) was added. The reaction mixture was warmed to rt, recooled to −78° C. over a period of 2 h and a neat solution of methyl iodide (5.68 g, 40 mmol) added. The reaction mixture was allowed to warm to rt overnight, quenched with saturated NH$_4$Cl (100 mL) at rt. It was extracted with EtOAc (100 mL). The organic phase was washed with brine (100 mL), dried (MgSO$_4$), and concentrated in vacuo to give a yellow oil which was crystallized from hexane to afford the product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (bs, 1H).

Step 1c: Preparation of 1-methylcyclopropylsulfonamide

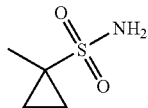

A solution of N-tert-butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield Example 3,1-methylcyclopropylsulfonamide, as a white solid (1.25 g, 96%): $^1$H NMR (CDCl$_3$) δ 0.84 (m, 2H), 1.41 (m, 2H), 1.58 (s, 3H), 4.65 (bs, 2H). Anal. Calcd. For C$_4$H$_9$NO$_2$S: C, 35.54; H, 6.71; N, 10.36. Found: C, 35.67; H, 6.80; N, 10.40.

Example 9

Preparation of 1-Propylcyclopropylsulfonamide

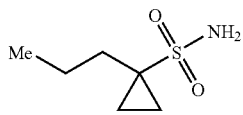

Steps 1b: Preparation of N-tert-Butyl-(1-benzyl)cyclopropyl-sulfonamide

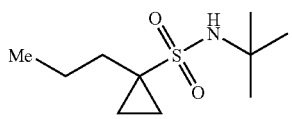

This compound was prepared using the process described for the preparation of 1-methylcyclopropylsulfonamide except propyl halide was utilized in place of methyl iodide in the second step of this process.

Example 10

Preparation of N-tert-Butyl-(1-allyl)cyclopropylsulfonamide

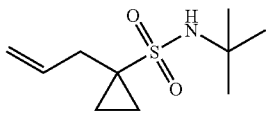

This compound, N-tert-Butyl-(1-allyl)cyclopropylsulfonamide, was obtained in 97% yield according to the procedure described in the synthesis of N-tert-Butyl-(1-methyl)cyclopropylsulfonamide except 1.25 equivalents of allyl bromide were used as electrophile. The compound was taken directly into the next reaction without purification: $^1$H NMR (CDCl$_3$) δ 0.83 (m, 2H), 1.34 (s, 9H), 1.37 (m, 2H), 2.64 (d, J=7.3 Hz, 2H), 4.25 (bs, 1H), 5.07-5.10 (m, 2H), 6.70-6.85 (m, 1H).

Preparation of 1-allylcyclopropylsulfonamide

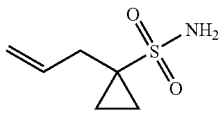

This compound, 1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromatography over SiO$_2$ using 2% MeOH in CH$_2$Cl$_2$ as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

Example 15

Preparation of Cyclopropylsulfonylamine Tert-Butyl Carbamate, a Key Intermediate in the Preparation of C1-Substituted cyclopropylsulfonamides

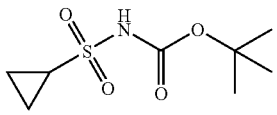

Step 1: Preparation of 3-chloropropylsulfonamide

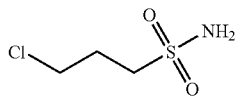

A solution of 3-chloropropanesulfonyl chloride (55 g, 310.7 mmol) was dissolved in THF (200 mL) and added dropwise over 30 minutes to a solution of NH$_4$OH (200 mL) cooled to 0° C. The reaction mixture was warmed to room temperature, stirred 1 hour, and the aqueous layer partioned multiple time with dichloromethane (4×500 mL). The combined dichloromethane layer was washed with 1N HCl (150 mL), water (150 mL), dried over MgSO$_4$, filtered, and concentrated in vacuo. The crude solid was recrystallized from the minimum amount of dichloromethane in hexanes to afford 3-chloropropylsulfonamide as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

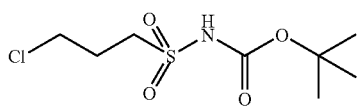

To a solution of 3-chloropropylsulfonamide (30.2 g, 191.5 mmol), triethylamine (30.2 mL, 217.0 mmol), and 4-DMAP (2.40 g, 19.6 mmol) in dichloromethane (350 mL) cooled to 0° C. was added slowly dropwise a solution of di-tert-butyl-dicarbonate (47.2 g, 216.9 mmol) in dichloromethane (250 mL) over 30 minutes. The reaction mixture was allowed to warm to room temperature, stirred an additional 3 hours and was partioned with 1N HCl (300 mL), water (300 mL), brine (300 mL), dried over MgSO$_4$, filtered, and concentrated in vacuo to afford the crude product. This material was triturated with 70 mL of 5% dichloromethane in hexanes to afford 3-chloropropylsulfonylamine tert-butylcarbamate as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of cyclopropylsulfonylamine tert-butyl carbamate

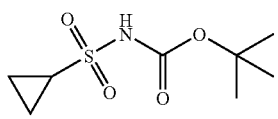

A solution of n-butyl lithium (74.7 mL, 119.5 mmol, 1.6M in hexane) was dissolved in dry THF (105 mL) and cooled to −78° C. under a Argon atmosphere. To this solution was added a solution of 3-chloropropylsulfonylamine tert-butyl-carbamate (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to afford the cyclopropylsulfonylamine tert-butyl carbamate as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

Example 16

Preparation of 1-methoxy-methylcyclopropyl-sulfonamide

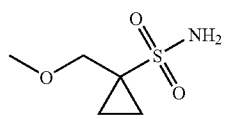

Step 1: Preparation of 1-methoxymethylcyclopropylsulfonylamine tert-butylcarbamate

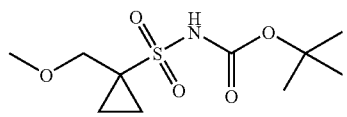

To a solution of cyclopropylsulfonylamine tert-butyl carbamate (1.0 g, 4.5 mmol) dissolved in THF (30 mL) cooled to −78° C., was added n-butyl lithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

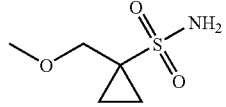

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

Example 17

Preparation of 1-cyclopropylmethylcyclopropylsulfonamide

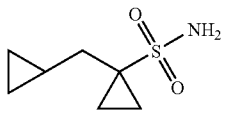

Step 1: Preparation of 1-cyclopropylmethylcyclopropylsulfonylamine tert-butylcarbamate

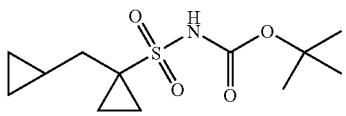

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethylcyclopropylsulfonamide

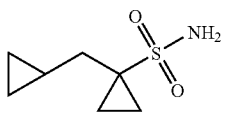

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromotography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

Example 19

Preparation of 1-(3,5-dimethylisoxazol-4-yl)carbamoylcyclopropanesulfonamide

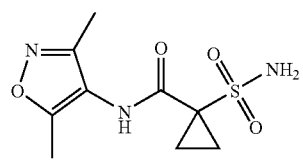

Step 1: Preparation of 1-(3,5-dimethylisoxazol-4-yl) carbamoylcyclopropanesulfonamide tert-butylcarbamate

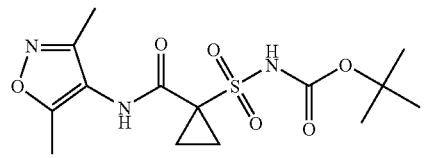

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl) carbamoylcyclopropanesulfonamide

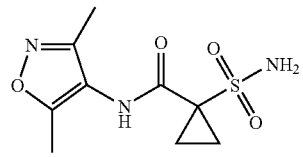

This compound was obtained in 50% yield (580 mg) from 1.62 g (4.52 mmol) of 1-(3,5-dimethylisoxazol-4-yl)carbamoylcyclopropanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30

(s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260(M$^+$+H).

Example 20

Preparation of Cyclobutylsulfonamide from Cylobutylbromide

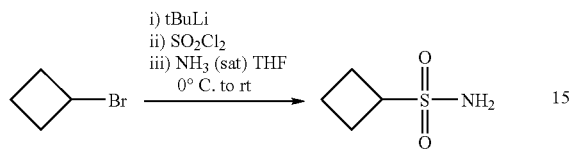

To a solution of 5.0 g (37.0 mmol) of cyclobutyl bromide in 30 mL of anhydrous diethyl ether (Et$_2$O) cooled to –78° C. was added 44 mL (74.8 mmol) of 1.7M tert-butyl lithium in pentanes and the solution slowly warmed to –35° C. over 1.5 h. This mixture was cannulated slowly into a solution of 5.0 g (37.0 mmol) of freshly distilled sulfuryl chloride in 100 mL of hexanes cooled to –40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1-2 drops of MeOH to afford 1.90 g (38%) of cyclobutylsulfonamide as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M–H)$^-$ calcd for C$_4$H$_8$NSO$_2$: 134.0276. found 134.0282.

Example 21

Preparation of Cyclopentyl Sulfonamide

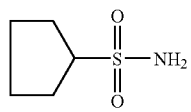

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to –78° C. The mixture was warmed to 0° C. over 1 h and was then carefully concentrated in vacuo. This mixture was redissolved in Et$_2$O (200 mL), washed once with some ice-cold water (200 mL), dried (MgSO$_4$) and concentrated carefully. This mixture was redissolved in 35 mL of THF, added dropwise to 500 mL of saturated NH$_3$ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH$_2$Cl$_2$ in hexanes with 1-2 drops of MeOH to afford 2.49 g (41%) of cyclopentylsulfonamide as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (bs, 2H); $^{13}$C NMR (CDCl$_3$) δ 25.90, 28.33, 63.54; MS m/e 148 (M–H)$^-$.

Example 22

Preparation of Cyclohexyl Sulfonamide

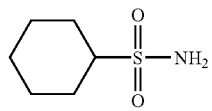

A solution of 18.5 mL (37.0 mmol) of 2M cyclohexylmagnesium chloride (TCI Americas) in ether was added dropwise to a solution of 3.0 mL (37.0 mmol) freshly distilled sulfuryl chloride in 100 mL of hexanes cooled to –78° C. The mixture was warmed to 0° C. over 1 h and was then carefully concentrated in vacuo. This mixture was redissolved in Et$_2$O (200 mL), washed once with some ice-cold water (200 mL), dried (MgSO$_4$) and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% EtOAc-hexanes as the eluent and was concentrated. The residue was recrystallized from the minimum amount of CH$_2$Cl$_2$ in hexanes with 1-2 drops of MeOH to afford 1.66 g (30%) of cyclohexyl-sulfonamide as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (bs, 2H); $^{13}$C NMR (CDCl$_3$) δ 25.04, 25.04, 26.56, 62.74; MS m/e 162 (M–1)$^-$.

Example 23

Preparation of Neopentylsulfonamide

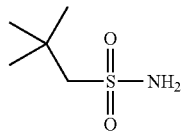

Following the procedure for the preparation of cyclohexylsulfonamide, 49 mL (37 mmol) of 0.75M neopentylmagnesium chloride (Alfa) in diethyl ether was converted to 1.52 g (27%) of neopentylsulfonamide as a white solid. $^1$H NMR (CDCl₃) δ 1.17 (s, 9H), 3.12 (s, 2H), 4.74 (brs, 2H); ¹³C NMR (CDCl₃) δ 29.46, 31.51, 67.38; MS m/e 150 (M−1)⁻.

Example 24

Preparation of Cyclobutylcarbinylsulfonamide

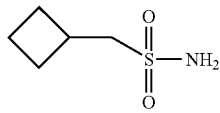

A solution of 12.3 g (83 mmol) of cyclobutylcarbinyl bromide (Aldrich) and 13.7 g (91 mmol) of sodium iodide in 150 mL of acetone was refluxed overnight and then cooled to room temperature. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether (diethyl ether) cooled to −78° C. was cannulated into a solution of 17 mL (21.98 mmol) of 1.3M sec-butyl lithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO₄), filtered, and concentrated carefully. This mixture was redissolved in 30 mL of THF, added dropwise to 500 mL of saturated NH₃ in THF and was allowed to stir overnight. The mixture was concentrated in vacuo to a crude yellow solid and was recrystallized from the minimum amount of dichloromethane in hexanes with 1-2 drops of methanol to afford 1.39 g (42%) of cyclobutyl carbinylsulfonamide as a white solid. ¹H NMR (CDCl₃) δ 1.81-2.03 (m, 4H), 2.14-2.28 (m, 2H), 2.81-2.92 (m, 1H), 3.22 (d, J=7 Hz, 2H), 4.74 (brs, 2H); ¹³C NMR (CDCl₃) δ 19.10, 28.21, 30.64, 60.93; MS m/e 148 (M−1)⁻.

Example 25

Preparation of Cyclopropylcarbinylsulfonamide

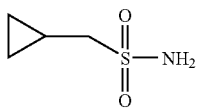

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). ¹H NMR (CDCl₃) δ 0.39-0.44 (m, 2H), 0.67-0.76 (m, 2H), 1.13-1.27 (m, 1H), 3.03 (d, J=7.3 Hz, 2H), 4.74 (brs, 2H); ¹³C NMR (CDCl₃) δ 4.33, 5.61, 59.93; MS m/e 134 (M−1).

Example 26

Preparation of 2-thiophenesulfonamide

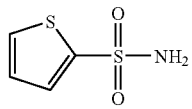

Prepared from 2-thiophenesulfonyl chloride (purchased from Aldrich) using the method of *Justus Liebigs Ann. Chem.*, 501, 1933, p. 174-182.

Example 27

Preparation of 4-bromobenzenesulfonamide

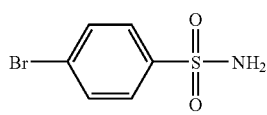

4-Bromophenylsulfonamide was prepared by treatment of commercially available 4-bromosulfonyl chloride with saturated ammonia in THF.

Example 28

Preparation of cyclopropanesulfonic acid (1-(R)-amino-2-(S)-vinyl-cyclopropanecarbonyl)amide HCl salt

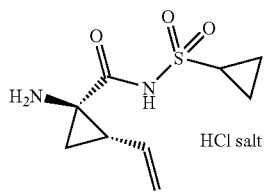

HCl salt

Step 1: Preparation of 1(R)-tert-butoxycarbonylamino-2(S)-vinylcyclopropanecarboxylic acid

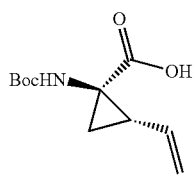

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl until pH 4 and extracted with ethyl acetate (3×40 mL). The combined organic extracts were washed with brine, dried (MgSO$_4$), filtered and concentrated to yield the title compound as a white solid (2.62 g, 87%). $^1$H NMR: (DMSO-d$_6$) δ 1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); MS m/z 228 (M$^+$+H).

Step 2: Preparation of cyclopropanesulfonic acid (1-(R)-tert-butoxycarbonylamino-2-(S)-vinylcyclopropanecarbonyl)-amide

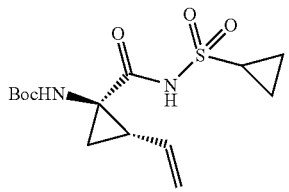

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and THF was concentrated in vacuo. The suspension was extracted with ethyl acetate (2×50 mL) and the combined organic extracts were dried (Na$_2$SO$_4$), filtered, and concentrated. Purification by recrystallization from hexanes-ethyl acetate (1:1) afforded the title compound (2.4 g) as a white solid. The mother liquor was purified by a Biotage 40S column (eluted 9% acetone in dichloromethane) to give a second batch of the title compound (1.1 g). Both batches were combined (total yield 92%). $^1$H NMR (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); MS m/z 331 (M$^+$+H).

Step 3: Preparation of cyclopropanesulfonic acid (1-(R)-amino-2-(S)-vinyl-cyclopropanecarbonyl) amide HCl salt

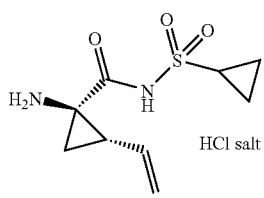

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1N HCl in diethyl ether (20 mL) and concentrated in vacuo. This procedure was repeated once. The resulting mixture was triturated from pentane and filtered to give the title compound as a hygroscopic, off-white solid (2.60 g, 92%). $^1$H NMR: (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); MS m/z 231 (M$^+$+H).

Example 29

Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid, Example 29

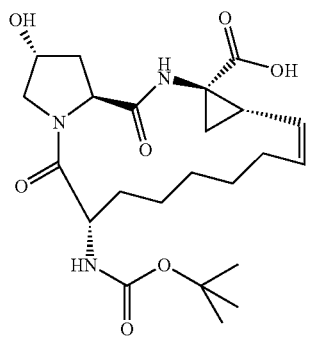

Example 29

Step 1: Preparation of 1-(2(S)-tert-Butoxycarbonylamino-non-8-enoyl)-4(R)-hydroxy-pyrrolidine-2(S)-carboxylic acid methyl ester

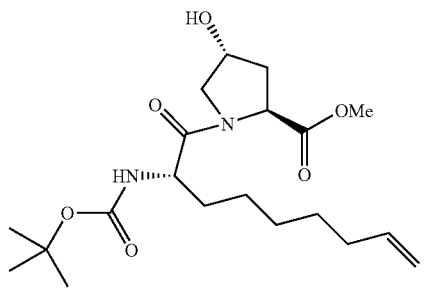

A solution of 2(S)-tert-butoxycarbonylamino-8-nonenoic acid (purchased from RSP Amino Acids) (3.5 g, 12.9 mmol) in 200 mL of DCM was treated sequentially with 4(R)-hydroxypyrrolidine-2(S)-carboxylic acid methyl ester hydrochloride (2.15 g, 11.8 mmol), N-methyl morpholine (4.25 mL, 38.6 mmol), and HATU (5.37 g, 14.1 mmol). The reaction mixture was stirred at rt under N$_2$ for 3 days, and then concentrated in vacuo. The residue was partitioned between ethyl acetate and pH 4 buffer (biphthalate). The organic phase was washed with sat. aq. NaHCO$_3$, dried (MgSO$_4$), and concentrated in vacuo to give the crude product. Flash chromatography (50% ethyl acetate/hexane to 100% ethyl acetate) gave 4.7 g (100%) of 1-(2(S)-tert-Butoxycarbonylamino-non-8-enoyl)-4(R)-hydroxy-pyrrolidine-2(S)-carboxylic acid methyl ester as a colorless oil: $^1$H NMR (500 MHz, $CD_3OD$) δ 1.33-1.50 (m, 8H), 1.46 (s, 9H), 1.57 (m, 1H), 1.72 (m, 1H) 2.08 (m, 2H), 2.28 (m, 1H), 3.72 (s, 3H,) 3.75-3.87 (m, 2H), 4.36 (m, 1H), 4.51 (bs, 1H), 4.57 (t, J=8.2 Hz, 1H), 4.95 (d, J=10.4 Hz, 1H), 5.01 (m, 1H), 5.83 (m, 1H); MS m/z 399 ($M^+$+1).

Step 2: Preparation of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester

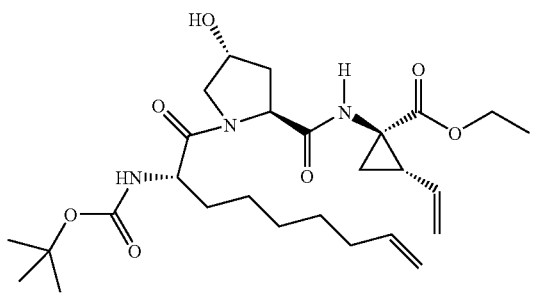

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at rt under $N_2$ for 16 h, and then concentrated in vacuo. The residue was partioned between ether and water. The ether phase was discarded, and the aqueous phase was treated with 1N HCl until the pH was 4. This acidic solution was extracted with EtOAc (3×). The combined EtOAc extracts were dried ($MgSO_4$) and concentrated in vacuo to give 4.36 g (96%) of 1-(2(S)-tert-butoxycarbonylamino-8-nonenoyl)-4(R)-hydroxy-pyrrolidine-2(S)-carboxylic acid as a white solid. This acid was then dissolved in 150 mL of DMF and (1R,2S)-1-amino-2-vinylcyclopropane carboxylic acid ethyl ester hydrochloride (2.61 g, 13.6 mmol), N-methyl morpholine (2.5 mL, 22.6 mmol), and HATU (5.2 g, 13.7 mmol) was added. The reaction mixture was stirred at rt under $N_2$ for 16 h, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give the crude product. Flash chromatography (60%-80% ethyl acetate/hexane) gave 6.0 g (98%) of 1-{[1-(2(S)-tert-Butoxycarbonylamino-non-8-enoyl)-4(R)-hydroxy-pyrrolidine-2(carbonyl]-(1R)-amino}-2(S)-vinyl-cyclopropanecarboxylic acid ethyl ester as a white solid: $^1$H NMR (500 MHz, $CD_3OD$) δ 1.25 (t, J=7.2 Hz, 3H), 1.33-1.80 (m, 10H), 1.46 (s, 9H), 2.09 (m, 3H), 2.25 (m, 2H), 3.76 (m, 2H), 4.14 (m, 2H), 4.27 (dd, J=8.5, 5.2 Hz, 1H), 4.50 (m, 2H), 4.94 (d, J=10.1 Hz, 1H), 5.01 (dd, J=17.1, 1.8 Hz, 1H), 5.11 (dd, J=10.4, 1.8 Hz, 1H), 5.30 (d, J=15.6 Hz, 1H), 5.80 (m, 2H), 8.57 (s, 1H); MS m/z 522 ($M^+$+1).

Step 3: Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid ethyl ester

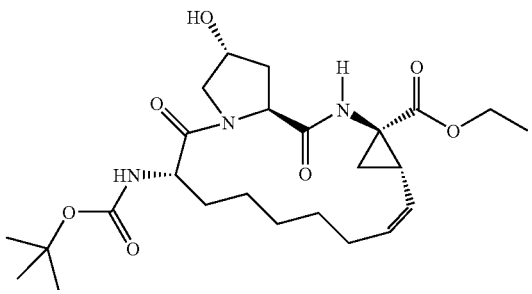

A solution of 1-{[1-(2(S)-tert-Butoxycarbonyl-amino-non-8-enoyl)-4(R)-hydroxy-pyrrolidine-2(S)carbonyl]-(1R)-amino}-2(S)-vinylcyclopropane-carboxylic acid ethyl ester (800 mg, 1.53 mmol) in 2 L of methylene chloride was flushed with $N_2$ for 0.5 h. Then tricyclohexylphosphine[1,3-bis(2,4,6-trimethyl-phenyl)-4,5-dihydroimidazol-2-ylidene][benzylidene]-ruthenium (IV) dichloride (Strem) (64 mg, 0.075 mmol) was added, and the mixture was flushed with $N_2$ for another 10 min. The light orange homogeneous solution was refluxed for 2 h to give a dark orange solution. The reaction mixture was cooled to rt and concentrated in vacuo to give an orange oil. Flash chromatography (ethyl acetate) gave 460 mg (61%) of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester as a gray solid. $^1$H NMR (500 MHz, $CDCl_3$) δ 1.19 (t, J=7.2 Hz, 3H), 1.42 (s, 9H), 1.22-1.8 (m, 8H), 1.87 (m, 2H), 2.03-2.22 (m, 4H), 2.63 (m, 1H), 3.65 (m, 1H), 4.09 (m, 3H), 4.45 (m, 1H), 4.56 (s, 1H), 4.82 (m, 1H), 5.23 (m, 1H), 5.51 (s, 1H), 7.16 (s, 1H); MS m/z 494 ($M^+$+1).

Step 4: (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid

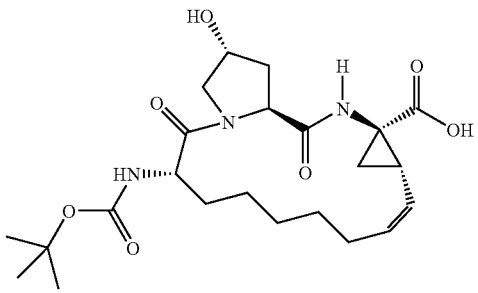

To a solution of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester (493 mg, 1.0 mmol) in THF (4 mL), methanol (1 mL), and water (2 mL), was added powdered lithium hydroxide (480 mg, 20 mmol), and the light yellow slurry stirred at rt under N₂ for 16 h. The mixture was then concentrated in vacuo and the residue partioned between ether and water. The ether phase was discarded, and the aqueous phase was treated with 1 N HCl until pH 4. This acidic solution was extracted with EtOAc three times. The combined EtOAc extracts were dried (MgSO₄) and concentrated in vacuo to give 460 mg (98%) of Example 18, (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid as a gray solid. $^1$H NMR (500 MHz, CD₃OD) δ ppm 1.26 (t, J=7.2 Hz, 3H), 1.35-1.52 (m, 15H), 1.57-1.68 (m, 3H), 1.79 (m, 1H), 2.04 (m, 1H), 2.16-2.41 (m, 3H), 3.80 (dd, J=10.7, 4.3 Hz, 1H), 3.88 (m, 1H), 4.38 (dd, J=8.9, 3.1 Hz, 1H), 4.55 (m, 2H), 5.39 (t, J=9.8 Hz, 1H), 5.58 (m, 1H); MS m/z 466 (M$^+$+1).

Example 30

Preparation of (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester Example 30

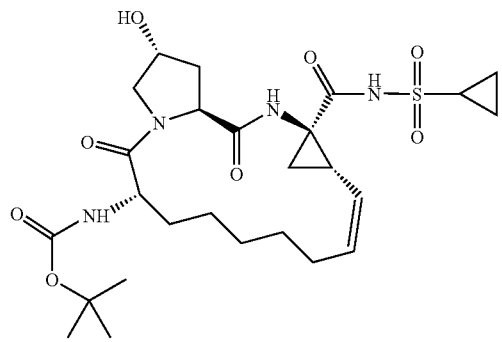

Step 1: Preparation of 1-{[1-(2-tert-Butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester

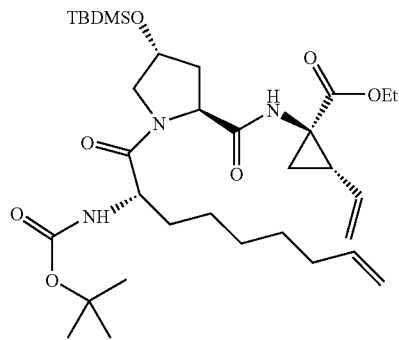

To a mixture of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester (1.5 g, 2.87 mmol.) in 10 mL of DMF was added imidazole (0.25 g, 3.67 mmol.) and tert-butyl-dimethylsilyl chloride (516 mg, 3.44 mmol.). The mixture was stirred at rt for two days. The reaction mixture was then concentrated in vacuo, and the residue was dissolved in ethyl acetate. This solution was washed with water, dried over magnesium sulfate, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester as a white solid.

$^1$H NMR (300 MHz, CD₃OD) δ 0.10 (s, 6H), 0.89 (s, 9H), 1.22 (m, 3H), 1.31-1.48 (m, 16H), 1.50-1.75 (m, 3H), 2.06 (m, 3H), 2.11-2.33 (m, 2H), 3.70 (m, 2H), 4.03-4.19 (m, 2H), 4.21 (m, 1H), 4.45 (t, J=7.87 Hz, 1H), 4.59 (m, 1H), 4.91 (d, J=9.15 Hz, 1H), 4.98 (d, J=17.20 Hz, 1H), 5.08 (dd, J=10.25, 1.83 Hz, 1H), 5.27 (dd, J=17.38, 1.65 Hz, 1H), 5.65-5.87 (m, 2H); MS m/z 636 (M$^+$+1).

Step 2: Preparation of 14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid, ethyl ester

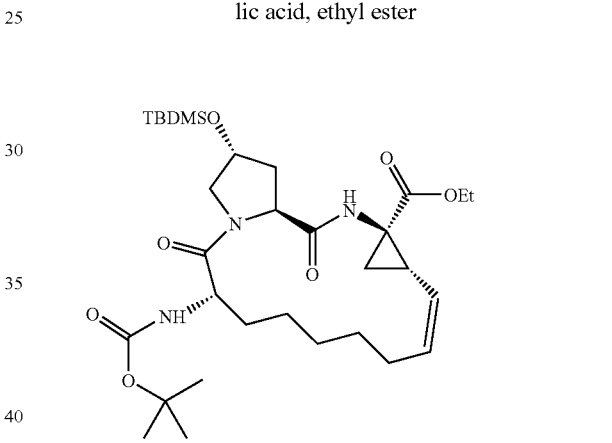

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmol.) in 640 mL of methylene chloride was added 215 mg (0.26 mmol.) of tricyclohexylphosphine[1,3-bis(2,4,6-tri[benzylidene]ruthenium(IV) dichloride. The mixture was heated at reflux for 15 min. The residue was concentrated in vacuo, and then purified by flash chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester as a white solid. $^1$H NMR (500 MHz, CD₃Cl) δ 0.06 (s, 3H), 0.07 (s, 3H), 0.86 (s, 9H), 1.18-1.24 (m, 6H), 1.34-1.64 (m, 14H), 1.86-1.96 (m, 3H), 2.02-2.09 (m, 1H), 2.11-2.17 (m, 1H), 2.19-2.28 (m, 1H), 2.57-2.63 (m, 1H), 3.50-3.54 (m, 1H), 3.71 (dd, J=10.22, 6.26 Hz, 1H), 4.06-4.17 (m, 2H), 4.52-4.58 (m, 2H), 4.75 (d, J=8.55 Hz, 1H), 5.21 (t, J=9.92 Hz, 1H), 5.35 (d, J=7.63 Hz, 1H), 5.45-5.50 (m, 1H), 6.94 (s, 1H); MS m/z 608 (M$^+$+1).

Step 3: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid

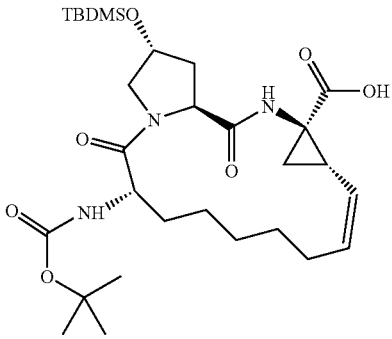

To a solution of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester (1.5 g, 2.47 mmol.) in a mixed solvent system of THF (4 mL), methanol (1 mL), and water (2 mL), was added powdered lithium hydroxide monohydrate (1.0 g, 50 mmol.). The light yellow slurry was stirred at rt under N$_2$ for 4 h. The mixture was then concentrated in vacuo, and the residue partioned between ether and water. The ether phase was discarded, and the aqueous phase was treated with 1 N HCl until reaching pH 4. This acidic solution was extracted with EtOAc (3×). The combined EtOAc extracts were dried (MgSO$_4$), and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid as an off-white solid. $^1$H NMR (300 MHz, CD$_3$OD) 0.12 (s, 6H), 0.89 (s, 9H), 1.23-1.64 (m, 17H), 1.70-1.87 (m, 1H), 1.90-2.49 (m, 6H), 3.70-3.80 (m, 1H), 3.83-3.90 (m, 1H), 4.28-4.36 (m, 1H), 4.47-4.55 (m, 1H), 4.65 (s, 1H), 5.30-5.39 (m, 1H), 5.53-5.62 (m, 1H); MS m/z 580 (M$^+$+1).

Step 4: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester

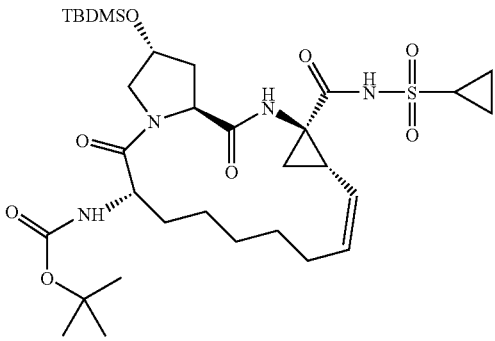

14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid (500 mg, 0.86 mmol.) was dissolved in 25 mL of THF and treated with CDI (180 mg, 1.12 mmol.). (Care was taken to avoid moisture by using oven dried glassware and maintaining a dry N2 atmosphere). After refluxing the reaction mixture for 2 h, it was cooled to rt and treated sequentially with cyclopropylsulfonamide (135 mg, 1.12 mmol.) and DBU (170 mg, 1.12 mmol.). The reaction mixture was stirred for 4 h at rt, and the THF was removed by rotary evaporation. The residue was partitioned between ethyl acetate and pH 4 buffer. The organic phase was dried (MgSO$_4$) and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester as a white solid. $^1$H NMR (300 MHz, CD$_3$OD) δ 1H 0.07 (s, 3H), 0.08 (s, 3H), 0.85 (s, 9H), 0.87-1.49 (m, 21H), 1.73-1.95 (m, 3H), 2.08-2.16 (m, 1H), 2.25-2.36 (m, 2H), 2.42-2.56 (m, 1H), 2.85-2.93 (m, 1H), 3.65-3.74 (dd, J=10.61, 3.66 Hz, 1H), 3.89 (d, J=10.25 Hz, 1H), 4.34 (m, J=9.70, 9.70 Hz, 1H), 4.43 (t, J=7.87 Hz, 1H), 4.57 (s, 1H), 4.94-5.01 (m, 1H), 5.10 (d, J=8.78 Hz, 1H), 5.66-5.75 (m, 1H), 6.55 (s, 1H), 10.13 (s, 1H); MS m/z 683 (M$^+$+1).

Step 5: Preparation of Example 19, (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester Example 30

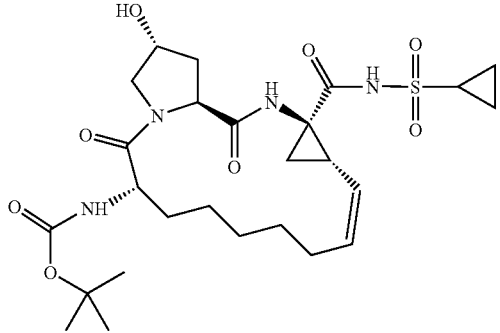

To a mixture of [18-(tert-butyl-dimethylsilanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester (330 mg, 0.48 mmol.) in 25 mL of THF was added tetrabutylammonium fluoride (150 mg, 0.54 mmol.). The reaction mixture was stirred at rt for 18 h, and then the THF was removed by rotary evaporation. The residue was partitioned between ethyl acetate and water. The organic phase was dried (MgSO$_4$) and concentrated in vacuo to give the crude product. It was then purified by triturating with hexane to yield 200 mg (73%) of (4-cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester, Example 19, as a white solid. $^1$H NMR (500 MHz, CD$_3$Cl) δ 1.87-1.64 (m, 21H), 1.70-1.98 (m, 3H), 2.15-2.56 (m, 5H), 2.85-2.94 (m, 1H), 3.71 (d, J=13.91 Hz, 1H), 4.10-4.26 (m, 2H), 4.51 (t, J=7.87 Hz, 1H), 4.62 (s, 1H), 4.98 (m, 1H), 5.06 (d, J=8.78 Hz, 1H), 5.64-5.71 (m, 1H), 6.72 (s, 1H), 10.24 (s, 1H); MS m/z 569 (M$^+$+1).

The following macrocyclic alcohol intermediates were prepared employing the procedures described in examples 29 and 30:

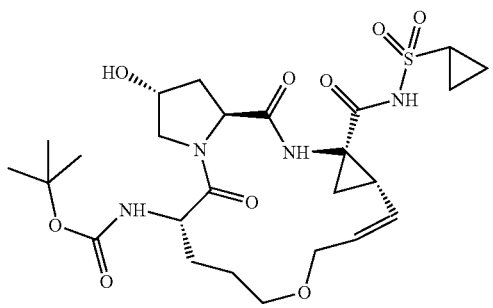
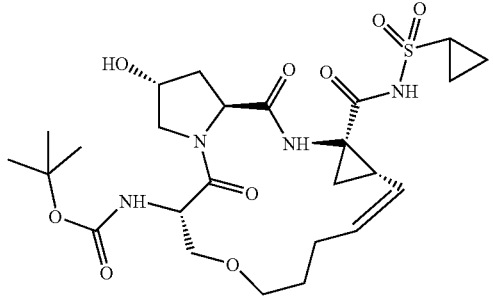
The following macrocyclic alcohol intermediates could be prepared employing the procedures described in examples 29 and 30:
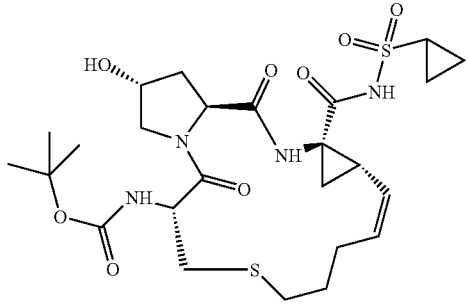
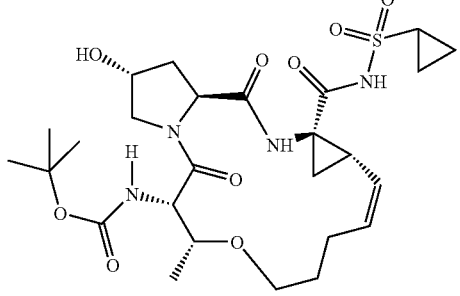
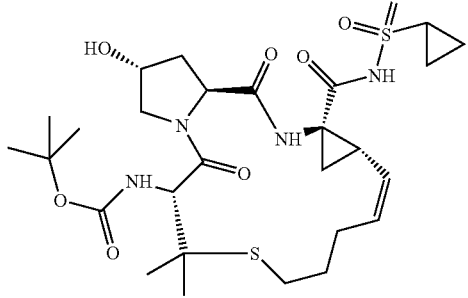
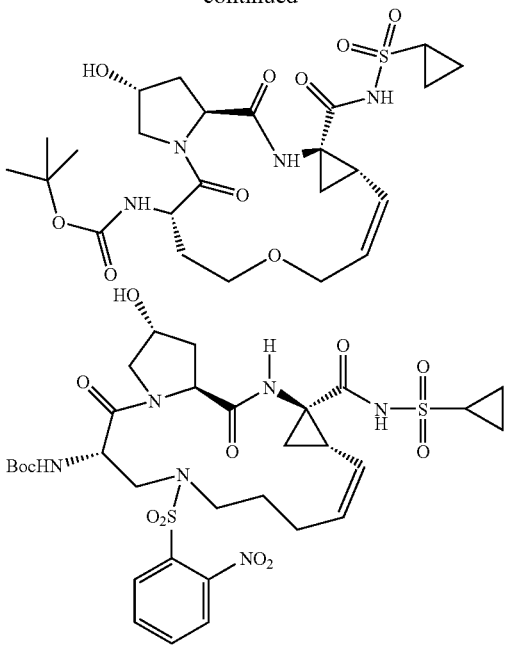
Example 31
Preparation of Example 31, 2(S)-tert-butoxycarbony-lamino-3-pent-4-enylsulfanylpropionic acid
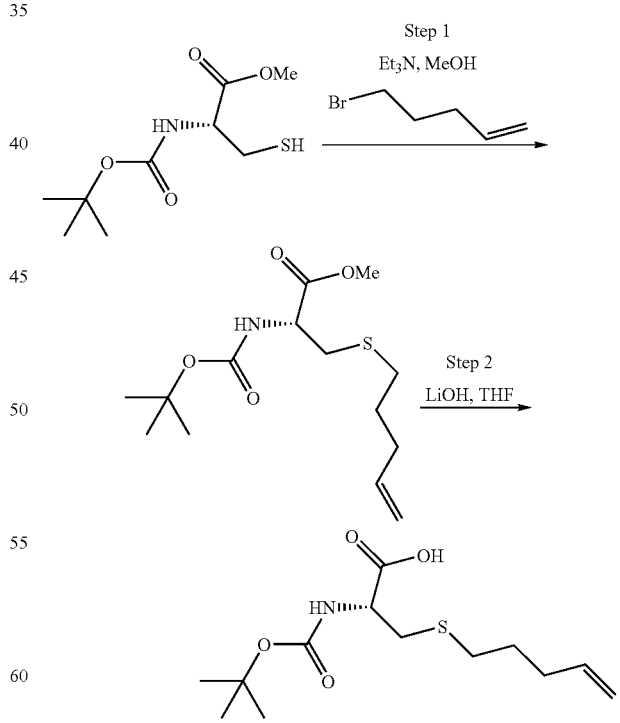
Example 31
Step 1: To a solution of N-Boc-cysteine methyl ester (3.36 g, 0.014 mol) in methanol (166 mL) at RT was added triethylamine (10.8 mL) and 1-bromopent-4-ene (3.19 g, 21 mmol, 1.5 equivalents) and the resulting solution was stirred at room temperature overnight. The mixture was then concentrated in vacuo and the resulting residual mixture was purified using flash chromatography (hexane, ethyl acetate gradient) to provide 1.76 g (41%) of the desired thioether. $^1$H NMR (500 MHz, CDCl$_3$) δ 1.43 (s, 9H), 1.64 (m, 2H), 2.11 (m, 2H), 2.51 (m, 2H), 2.95 (m, 2H), 3.75 (s, 3H), 4.51 (m, 1H), 4.95-5.03 (m, 2H), 5.34 (m, 1H), 5.80 (1H, m); MS m/z 304(M$^+$+1).

Step 2: The thioether product of step 1 (9.51 g, 31.4 mmol) was added to a mixture of 1M LiOH in water (200 mL) and THF (200 mL) and the resulting mixture was stirred at room temperature overnight. The reaction mixture was then acidified using 1N hydrochloric acid and the resulting mixture was extracted several times with ethyl acetate. The extracts were combined, dried over magnesium sulfate, and concentrated in vacuo to provide the desired acid, Example 20, which was used as is in the next reaction.

Example 32

Preparation of Example 32, N-tert-Butoxycarbonyl-3-(4-pentenylthio)-L-valine

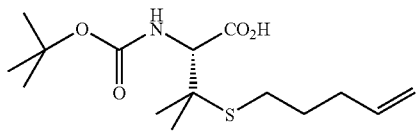

Example 32

Step 1: Preparation of N-tert-butoxycarbonyl-3-(4-pentenylthio)-L-valine, methyl ester

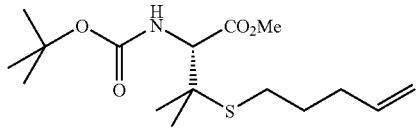

To a solution of 7.12 g (48 mmol, 1.0 eq) of L-penicillamine in 100 mL of 1,4-dioxane and 25 mL of water at room temperature was added 9.60 mL (96 mmol, 2.0 eq) of 10N aqueous sodium hydroxide solution, followed by the dropwise addition of 12.00 mL (101 mmol, 2.1 eq) of 5-bromo-1-pentene over several minutes. The resulting mixture was stirred at room temperature for 68 hours. At this point 12.50 g (57 mmol, 1.2 eq) of di-tert-butyl dicarbonate was added, and the mixture was stirred at room temperature for another 6 hours. The mixture was concentrated under vacuum, and the residue was dissolved in water. The aqueous mixture was washed with diethyl ether, adjusted to pH 3 employing 1N hydrochloric acid, and then extracted with ethyl acetate. The combined extracts were washed with brine, dried over anhydrous magnesium sulfate, filtered, and concentrated under vacuum. The crude product (12.20 g) was dissolved in 120 mL of anhydrous dimethylsulfoxide. To this solution was added 10.50 g (76 mmol) of potassium carbonate and 4.70 mL (76 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 8.54 g of N-tert-butoxycarbonyl-3-(4-pentenylthio)-L-valine, methyl ester as a colorless oil. NMR (300 MHz, CDCl$_3$): δ 5.76 (d of d of t, 1H, J=17.2, 10.3, 6.6 Hz), 5.35 (br d, 1H, J=9.0 Hz), 5.05-4.94 (m, 2H), 4.27 (br d, 1H, J=9.0 Hz), 3.73 (s, 3H), 2.52 (m, 2H), 2.13 (quart., 2H, J=7.3 Hz), 1.61 (quint., 2H, J=7.3 Hz), 1.43 (s, 9H), 1.35 (s, 3H), 1.33 (s, 3H).

Step 2: Preparation of Example 32, N-tert-Butoxycarbonyl-3-(4-pentenylthio)-L-valine

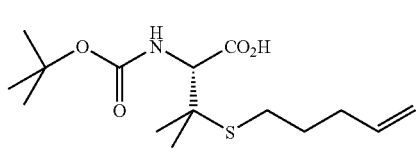

Example 32

To a solution of 8.52 g (25.7 mmol) of N-tert-butoxycarbonyl-3-(4-pentenylthio)-L-valine, methyl ester in 200 mL of tetrahydrofuran at room temperature was added a solution of 1.10 g (26.2 mmol) of lithium hydroxide monohydrate in 50 mL of water. The resulting mixture was stirred at room temperature for 65 hours. To the reaction mixture then was added 28 mL of 1.00N hydrochloric acid. The mixture was diluted with diethyl ether, washed with water (3×) and brine, dried over anhydrous sodium sulfate, filtered, and concentrated under vacuum to afford 8.10 g of N-tert-butoxycarbonyl-3-(4-pentenylthio)-L-valine as a colorless oil. NMR (300 MHz, CDCl$_3$): δ 5.75 (d of d of t, 1H, J=17.2, 10.3, 6.6 Hz), 5.40 (br s, 1H), 5.05-4.94 (m, 2H), 4.28 (br s, 1H), 2.56 (m, 2H), 2.13 (quart., 2H, J=7.3 Hz), 1.63 (quint., 2H, J=7.3 Hz), 1.44 (s, 9H), 1.39 (s, 3H), 1.37 (s, 3H).

Example 33

Preparation of Example 33, 5-Allyloxy-2(S)-(tert-butoxycarbonylamino)pentanoic acid

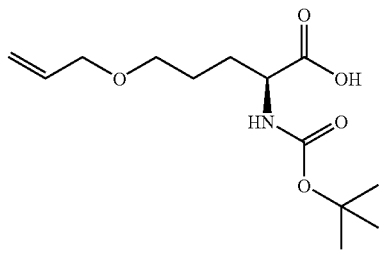

Example 33

Step 1: Preparation of Isopropylpyrrolidin-5-one-2(S)-carboxylate

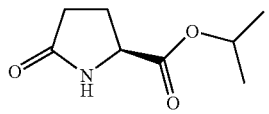

A solution of L-pyroglutamic acid (Aldrich, 25.0 g, 195 mmol) and para-toluenesulfonic acid mono hydrate (3.71 g, 19.5 mmol) was refluxed in isopropanol (40 mL) under nitrogen for 6 hours using a Dean-Stark trap variation (condensate returned through a Soxhlet extractor filled with 4 Å molecular sieves). After cooling to room temperature, the reaction was diluted with ether, washed with saturated aqueous sodium bicarbonate and then saturated aqueous NaCl, dried (MgSO$_4$) and evaporated to give a colorless syrup. It crystallized upon setting. Triturating the crystalline residue in hexane provided 31.9 g (96%) of isopropyl pyrrolidin-5-one-2(S)-carboxylate as white prisms: $^1$H NMR (300 MHz, Chloroform-D) δ 6.35 (br s, 1H), 5.04 (sept. 1H, J=6.2 Hz), 4.18 (dd, 1H, J=8.4, 5.3 Hz), 2.51-2.28 (m, 3H), 2.27-2.12 (m, 1H), 1.24 (d, 6H, J=6.2 Hz). LCMS m/z 172 (M+H)$^+$.

Step 2: Preparation of Isopropyl 1-(tert-butoxycarbonyl)-pyrrolidin-5-one-2(S)-carboxylate

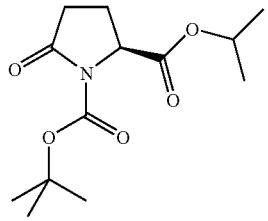

A solution of isopropyl pyrrolidin-5-one-2(S)-carboxylate (product of step 26A, 31.9 g, 188 mmol), di-tert-butyl dicarbonate (48.6 g, 225 mmol) and DMAP (2.30 g, 8.8 mmol) in acetonitrile (300 mL) was stirred at room temperature under N$_2$ for 30 minutes. The reaction was evaporated to about 100 mL, diluted with ether, washed with 1N HCl then saturated aqueous NaCl, dried (MgSO$_4$) and evaporated to give isopropyl 1-(tert-butoxycarbonyl)pyrrolidin-5-one-2(S) carboxylate as a light yellow oil, 50.1 g (99%): $^1$H NMR (300 MHz, Chloroform-D) δ 5.06 (sept. 1H, J=6.2 Hz), 4.53 (dd, 1H, J=9.5, 2.9 Hz), 2.66-2.40 (m, 2H), 2.36-2.22 (m, 1H), 2.03-1.93 (m, 1H), 1.47 (s, 9H), 1.26 (d, 3H, J=6.2 Hz), 1.24 (d, 3H, J=6.2 Hz). LCMS m/z 272 (M+H)$^+$.

Step 3: Preparation of Isopropyl 2(S)-(tert-butoxycarbonylamino)-5-hydroxypentanoate

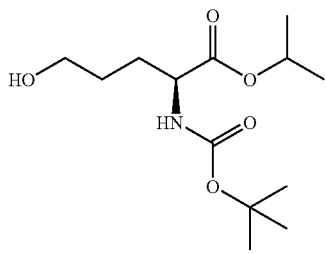

To a solution of isopropyl 1-(tert-butoxycarbonyl)pyrrolidin-5-one-2(S)-carboxylate (product of step 26B, 49.5 g, 183 mmol) in methanol (300 mL) was added sodium borohydride (10.0 g, 263 mmol) in ~1 g portions over 1.5 hours. The reaction was stirred under nitrogen for another 10 minutes. It was diluted with water, extracted with ether, combined organic fractions washed with saturated aqueous NaCl, dried (MgSO$_4$) and evaporated to give a light yellow oil. Flash chromatography (silica gel, 20-30% ethyl acetate/hexane) gave 31.8 g (64%) of isopropyl 2(S)-(tert-butoxycarbonylamino)-5-hydroxypentanoate as a colorless syrup: $^1$H NMR (300 MHz, Chloroform-D) δ 5.16 (br d, 1H, J=7.3 Hz), 5.03 (sept., 1H, J=6.2 Hz), 4.28 (br d, 1H, J=6.2 Hz), 3.67 (br dd, J=10.2, 5.5 Hz), 1.94-1.79 (m, 2H), 1.76-1.67 (m, 1H), 1.66-1.56 (m, 2H), 1.43 (s, 9H), 1.25 (d, 3H, J=6.2 Hz), 1.23 (d, 3H, J=6.2 Hz). LCMS m/z 276 (M+H)$^+$.

Step 4: Preparation of Isopropyl-5-allyloxy-2(S)-(tert-butoxycarbonylamino)pentanoate

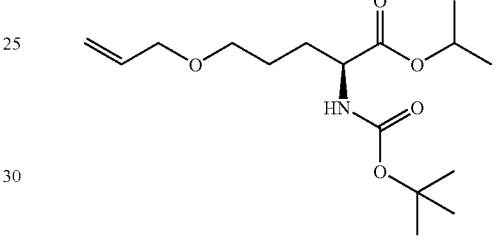

A degassed mixture of isopropyl 2(S)-(tert-butoxycarbonylamino)-5-hydroxypentanoate (product of step 26C, 17.6 g, 63.9 mmol), allyl methyl carbonate (24.0 ml, 213 mmol), Pd$_2$(dba)$_3$ (1.62 g, 1.78 mmol) and BINAP (4.42 g, 7.10 mmol) in THF (150 mL) was refluxed under nitrogen for 3 hours. After cooling to room temperature, the reaction was diluted with ether, filtered through celite and evaporated giving a dark brown syrup. Flash chromatography of the residue (silica gel, 30% ether/hexane) gave isopropyl 5-allyloxy-2 (S)-(tert-butoxycarbonylamino)pentanoate as a viscous colorless oil, 16.3 g (81%): $^1$H NMR (300 MHz, Chloroform-D) δ 5.88 (ddt, 1H, 17.4, 10.4, 5.5), 5.28 (m, 1H), 5.22-5.11 (m, 1H), 5.02 (sept., 1H, J=6.2 Hz), 4.21 (br t, 1H, J=6.7 Hz), 3.94 (dt, 2H, J=5.9, 1.5 Hz), 3.42 (t, 2H, J=5.9 Hz), 1.90-1.82 (m, 1H), 1.75-1.57 (m, 3H), 1.42 (s, 9H), 1.21 (d, 3H, J=6.2 Hz), 1.19 (d, 3H, J=6.2 Hz). LCMS m/z 316 (M+H)$^+$.

Step 5: Preparation of Example 33, 5-Allyloxy-2(S)-(tert-butoxycarbonylamino)pentanoic acid Example 33

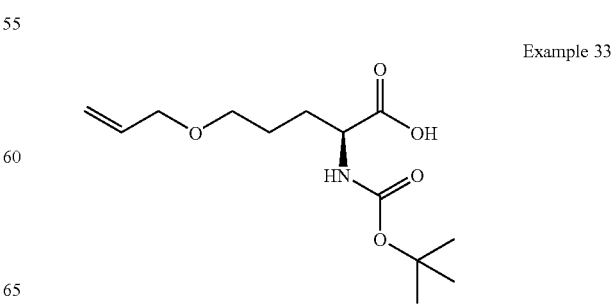

A mixture of isopropyl 5-allyloxy-2(S)-(tert-butoxycarbonylamino)pentanoate (product of step 26D, 16.1 g, 51.1 mmol) and lithium hydroxide hydrate (4.19 g, 102 mmol) in THF/water (100 mL/20 mL) was stirred at room temperature under nitrogen for 16 hours. The reaction was diluted with water, washed with ether, pH of aqueous fraction adjusted to ~4, extracted with ether, combined organic fractions washed with saturated NaCl, dried (MgSO₄) and evaporated giving 5-allyloxy-2(S)-(tert-butoxycarbonylamino)pentanoic acid as a light yellow syrup: ¹H NMR (300 MHz, Chloroform-D) δ 5.89 (ddt, 1H, J=17.4, 10.4, 5.5), 5.25 (dd, 1H, J=17.4, 1.6 Hz), 5.17 (dd, 1H, J=10.4, 1.6 Hz), 4.30 (br d, 1H, J=6.2), 3.96 (dt, 2H, J=5.9, 1.5 Hz), 3.46 (t, 2H, J=5.9 Hz), 1.96-1.86 (m, 1H), 1.85-1.77 (m, 1H), 1.75-1.64 (m, 2H), 1.43 (s, 9H). LCMS m/z 274 (M+H)⁺.

Example 34

General Procedure for the Preparation of Example 34

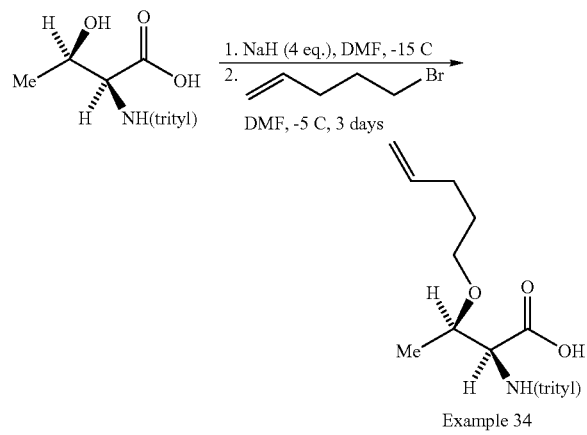

Example 34

Example 23 was prepared by adding a DMF solution of N-trityl protected threonine to a DMF solution of sodium hydride cooled to −15 C. The reaction mixture was stirred for 30 minutes at −15 C after which 5-bromo-1-pentene was added and the resulting mixture was warmed to −5 C. The reaction mixture was maintained at −5 C for 3 days after which time the reaction was quenched by the addition of 1N aqueous HCl and worked up using standard extraction procedures as described above. Example 23 was obtained in pure form by standard chromatography procedures.

Example 35

Preparation of Example 35, N-tert-Butoxycarbonyl-O-(4-pentenyl)-L-serine

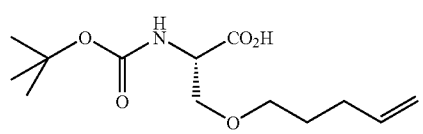

Example 35

Step 1: Preparation of N-tert-Butoxycarbonyl-O-(4-pentenyl)-L-serine, methyl ester

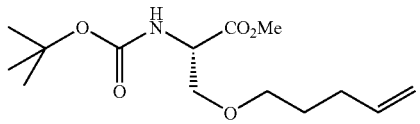

To a solution of 10.26 g (50 mmol, 1.0 eq) of N-tert-butoxycarbonyl-L-serine in 500 mL of anhydrous dimethylsulfoxide at room temperature was added 2.00 g (50 mmol, 1.0 eq) of 60% sodium hydride in mineral oil. This mixture was stirred at room temperature for 0.5 hour until the evolution of gas had ceased. To the resulting solution was added 6.00 mL (50 mmol, 1.0 eq) of 5-bromo-1-pentene followed immediately by another 2.00 g (50 mmol, 1.0 eq) of 60% sodium hydride in mineral oil. The reaction mixture then was stirred at room temperature for 16 hours. The mixture was diluted with 200 mL of water, adjusted to pH 3-4 by the addition of 50 mL of 1.00N hydrochloric acid, and extracted with ethyl acetate. The organic phase was washed with water (2×) and brine, dried over anhydrous sodium sulfate, filtered, and concentrated under vacuum. To remove the residual mineral oil the resulting material was dissolved in a dilute aqueous sodium hydroxide solution. This aqueous solution was washed with hexane and then adjusted to pH 4 employing hydrochloric acid, and extracted with ethyl acetate. The extract was washed with water (2×) and brine, dried over anhydrous sodium sulfate, filtered, and concentrated under vacuum.

The crude product (7.70 g) was dissolved in 100 mL of anhydrous dimethylsulfoxide. To this solution was added 7.80 g (56 mmol) of potassium carbonate and 3.50 mL (56 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 6.70 g of N-tert-butoxycarbonyl-O-(4-pentenyl)-L-serine, methyl ester as a colorless oil. NMR (300 MHz, CDCl₃): δ 5.78 (d of d of t, 1H, J=17.2, 10.2, 6.6 Hz), 5.34 (br d, 1H, J=8.0 Hz), 5.03-4.92 (m, 2H), 4.40 (m, 1H), 3.81 (d of d, 1H, J=9.5, 2.9 Hz), 3.74 (s, 3H), 3.61 (d of d, 1H, J=9.5, 3.5 Hz), 3.42 (m, 2H), 2.06 (quart., 2H, J=7.3 Hz), 1.61 (quint., 2H, J=7.3 Hz), 1.44 (s, 9H).

Step 2: Preparation of Example 35, N-tert-Butoxycarbonyl-O-(4-pentenyl)-L-serine

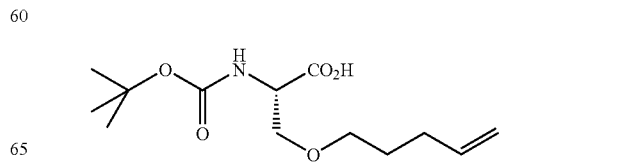

Example 35

To a solution of 6.65 g (23 mmol) of N-tert-butoxycarbonyl-O-(4-pentenyl)-L-serine, methyl ester in 500 mL of tetrahydrofuran at room temperature was added a solution of 1.95 g (46 mmol) of lithium hydroxide monohydrate in 100 mL of water. The resulting mixture was stirred at room temperature for 40 hours. To the reaction mixture then was added 46 mL of 1.00N hydrochloric acid. The mixture was diluted with ethyl acetate, washed with water (3×) and brine, dried over anhydrous sodium sulfate, filtered, and concentrated under vacuum to afford 6.30 g of N-tert-butoxycarbonyl-O-(4-pentenyl)-L-serine as a colorless oil. NMR (300 MHz, CDCl$_3$): δ 5.77 (d of d of t, 1H, J=17.2, 10.2, 6.6 Hz), 5.37 (br d, 1H, J=8.0 Hz), 5.03-4.92 (m, 2H), 4.42 (m, 1H), 3.87 (d of d, 1H, J=9.5, 2.6 Hz), 3.63 (d of d, 1H, J=9.5, 4.0 Hz), 3.45 (t, 2H, J=6.6 Hz), 2.07 (quart., 2H, J=7.3 Hz), 1.64 (quint., 2H, J=7.3 Hz), 1.44 (s, 9H).

Example 36

Preparation of Example 36, (S)-4-allyloxy-2-(tert-butoxycarbonylamino)butyric acid

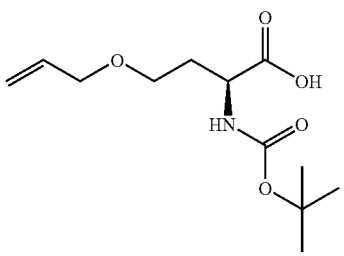

Example 36

To a mixture of sodium hydride (913 mg, 22.8 mmol.) in DMF at 0° C. was added N-t-Boc-L-homoserine (2 g, 9.13 mmol.). This reaction mixture was stirred at 0° C. for 15 min, and then allyl bromide (1.38 g, 11.4 mmol.) was added. The mixture was warmed up to rt, and stirred for 2 h. It was then concentrated in vacuo. The residue was diluted with water, and sequentially washed with hexane and ether. The organic layers were discarded, and the aqueous layer was carefully adjusted to pH 3 with 1 N HCl. This acidic aqueous solution was extracted with ethyl acetate. The organic phase was dried (MgSO$_4$), and concentrated in vacuo to yield 2.2 g (93%) of (S)-4-allyloxy-2-(tert-butoxycarbonylamino)butyric acid as a colorless oil. $^1$H NMR (300 MHz, CD$_3$OD) δ 1.42 (s, 9H), 1.80-1.90 (m, 1H), 2.04-2.16 (m, 1H), 3.50-3.54 (m, 2H), 3.97 (d, J=4.39 Hz, 2H), 4.23 (dd, J=8.78, 4.39 Hz, 1H), 5.15 (d, J=10.25 Hz, 1H), 5.26 (dd, J=17.38, 1.65 Hz, 1H), 5.84-5.97 (m, 1H).

Example 37

Preparation of Example 37, (S)-2-(tert-butoxycarbonyl)-3-(2-nitro-N-(pent-4-enyl)phenylsulfonamido)propanoic acid

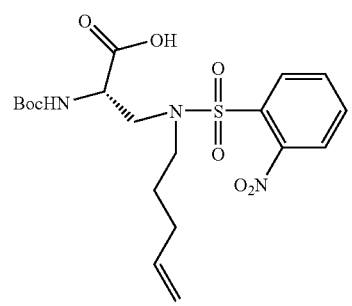

Example 37

Step 1: Preparation of methyl 3-amino-2(S)-(tert-butoxycarbonylamino)propanoate

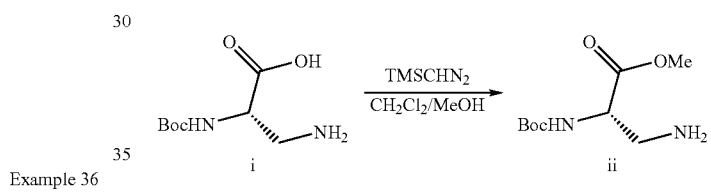

To a mixture of i (Boc-DAP-OH) (3.0 g 14.7 mmol) in 50 mL of methylene chloride was added 5 mL of methanol. To this solution was slowly added (trimethylsilyl)diazomethane (2 M in ether, 7.9 mL, 15.8 mmol.). The mixture was stirred at rt for 2 h until all of the solid dissolved and the solution turned light yellow. It was then concentrated to yield 3.2 g (99%) of methyl 3-amino-2(S)-(tert-butoxycarbonylamino)propanoate ii as a colorless oil. $^1$H NMR (CD$_3$OD, 300 MHz) δ 1.46 (s, 9H), 2.82-3.00 (m, 2H), 3.71 (s, 3H), 4.14 (brs, 1H).

Preparation of methyl 2(S)-(tert-butoxycarbonylamino)-3-(2-nitrophenylsulfonamido)propanoate iii

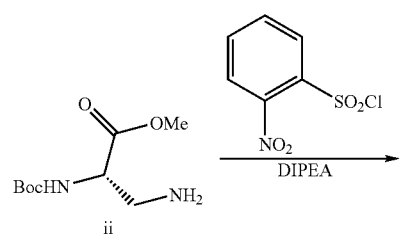

-continued

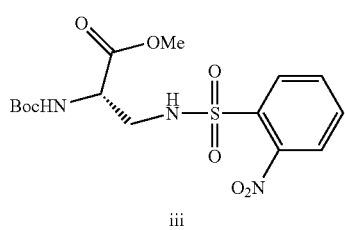

iii

To a mixture of methyl 3-amino-2(S)-(tert-butoxycarbonylamino)propanoate ii (1.6 g, 7.3 mmol.) in DCM (50 mL) was added DIPEA (1.64 mL, 9.4 mmol.) and 2-nitrobenzene sulfonyl chloride (1.62 g, 7.3 mmol.). The mixture was stirred at rt for 2 h. It was then concentrated, dissolved in ethyl acetate, which was then washed with sat. sodium bicarbonate, brine and dried over magnesium sulfate. It was then filtered, concentrated to yield 2.9 g (98%) of methyl 2(S)-(tert-butoxycarbonylamino)-3-(2-nitrophenylsulfonamido)propanoate iii as a yellow foam. $^1$H NMR (CD$_3$OD, 300 MHz) δ 1.41 (s, 9H), 3.36-3.51 (m, 2H), 3.71 (s, 3H), 4.22 (m, 1H), 7.80-7.90 (m, 3H), 8.07-8.10 (m, 1H).

Preparation of methyl 2(S)-(tert-butoxycarbonylamino)-3-(2-nitro-N-(pent-4-enyl)phenylsulfonamido)propanoate iv

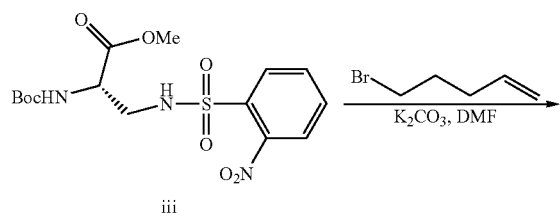

iii

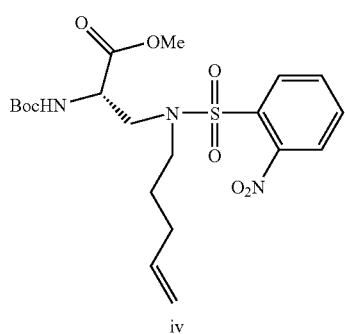

iv

To a mixture of methyl 2(S)-(tert-butoxycarbonylamino)-3-(2-nitrophenylsulfonamido)propanoate iii (150 mg, 0.37 mmol) in 3 mL of DMF was added potassium carbonate (102 mg, 0.74 mmol.). This mixture was stirred at rt for 20 min followed by the addition of 5-bromo-1-pentene (65 □L, 0.55 mmol.). The reaction mixture was stirred at rt for 2 days. It was then filtered, concentrated and purified by silica gel chromatography (eluting with 25% ethyl acetate in hexane) to give 75 mg (43%) of methyl 2(S)-(tert-butoxycarbonylamino)-3-(2-nitro-N-(pent-4-enyl)phenylsulfonamido)propanoate iv as a yellow solid. $^1$H NMR (CD$_3$OD, 300 MHz) δ 1.42 (s, 9H), 1.54-1.64 (m, 2H), 1.97 (q, J=7.20 Hz, 2H), 3.37 (m, 2H), 3.57-3.80 (m, 2H), 3.72 (s, 3H), 4.42 (dd, J=8.60, 5.31 Hz, 1H), 4.91-5.01 (m, 2H), 5.69-5.79 (m, 1H), 7.75-7.85 (m, 3H), 8.04 (m, 1H); MS m/z 372 (M$^+$+1-Boc).

Preparation of Example 37, 2(S)-(tert-butoxycarbonylamino)-3-(2-nitro-N-(pent-4-enyl)phenylsulfonamido)propanoic acid v

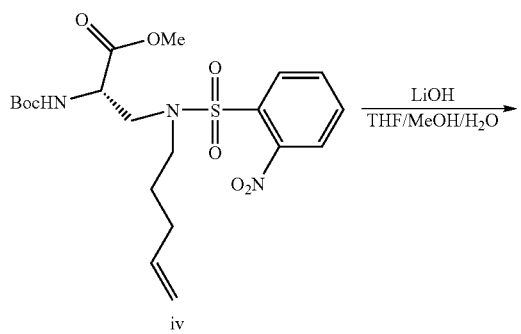

iv

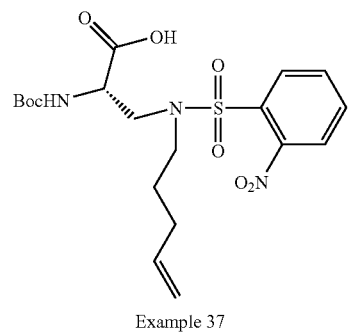

Example 37

(S)-methyl 2-(tert-butoxycarbonyl)-3-(2-nitro-N-(pent-4-enyl)phenylsulfonamido)-propanoate iv (500 mg, 1.06 mmol) was dissolved in the mixed solvent system: THF (4 mL), methanol (1 mL), and water (2 mL). Powdered lithium hydroxide (250 mg, 10.4 mmol) was added. The light yellow slurry was stirred at rt for 15 h, and then concentrated in vacuo. The residue was partitioned between ether and water. The ether phase was discarded, and the aqueous phase was treated with 1 N HCl until the pH was 4. This acidic solution was extracted with ethyl acetate four times. The combined ethyl acetate extracts were dried (MgSO$_4$) and concentrated in vacuo to give 430 mg (89%) of 2-(tert-butoxycarbonylamino)-3-(2-nitro-N-(pent-4-enyl)phenylsulfonamido)propanoic acid (Example 26) as a yellow oil. $^1$H NMR (CD$_3$OD, 300 MHz) δ 1.38 (s, 9H), 1.51-1.60 (m, 2H), 1.89-1.98 (m, 2H), 3.28-3.32 (m, 2H), 3.59-3.64 (dd, J=14.95, 9.46 Hz, 1H), 3.71-3.74 (m, 1H), 4.33 (dd, J=9.61, 4.43 Hz, 1H), 4.87-4.94

(m, 2H), 5.63-5.72 (m, 1H), 7.71-7.77 (m, 3H), 8.01 (dd, J=7.48, 1.37 Hz, 1H); MS m/z 358 (M⁺+1-Boc).

Example 86

Preparation of (1S,4R,6S,14S,18R)-[7-cis-4-Cyclopropanesulfonylaminocarbonyl-12-cyclopropyl-18-hydroxy-2,15-dioxo-3,12,16-triaza-tricyclo[14.3.0.0⁴,⁶]nonadec-7-en-14-yl]carbamic acid, tert-butyl ester (Example 86)

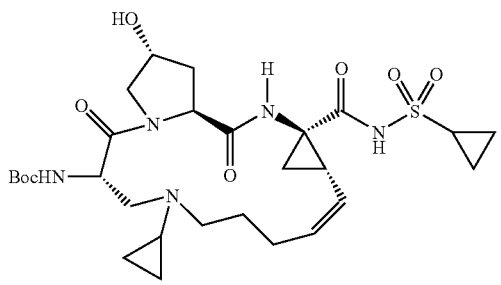

Example 86

Step 1: Synthesis of N-(pent-4-enyl)cyclopropanamine

Using an addition funnel, a solution of 5-bromopentene (15.75 g, 106 mmol) in 50 mL of methanol was added over the course of 5 min to a solution of cyclopropylamine (20.6 g, 361 mmol) in 200 mL of methanol. This solution was allowed to stir at rt for 72 h at which time is was refluxed for 1 h. The methanol and excess cyclopropylamine were removed by distillation. The residue, hydrobromide salt of the product, was partitioned between ether and 4 N NaOH. The aqueous phase was washed with ether (2×). The combined ether extracts were dried (MgSO₄), filtered, and concentrated to give 8 g (60%) of N-(pent-4-enyl)cyclopropanamine as a yellow oil: ¹H NMR (500 MHz, CDCl₃) δ 0.31-0.36 (m, 2H) 0.40-0.46 (m, 2H) 1.53-1.63 (m, 2H) 1.87 (brs, 1H) 2.05-2.10 (m, 2H) 2.10-2.14 (m, 1H) 2.69 (t, J=7.32 Hz, 2H) 4.91-5.07 (m, 2H) 5.72-5.88 (m, 1H).

Step 2: Synthesis of 2(S)-(tert-butoxycarbonylamino)-3-[N-cyclopropyl-N-(pent-4-enyl)amino]propanoic acid

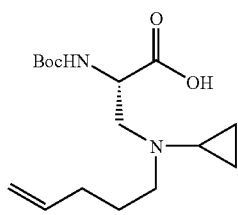

N-(Pent-4-enyl)cyclopropanamine (668 mg, 5.30 mmol) in 20 mL of acetonitrile was added to a slurry of N-t-butoxycarbonyl-L-serine β-lactone (1.0 g, 5.30 mmol) in 40 mL of acetonitrile. The mixture was stirred under N₂ at rt for 5 days, and then concentrated in vacuo to give crude 2(S)-(tert-butoxycarbonylamino)-3-[N-cyclopropyl-N-(pent-4-enyl)amino]propanoic acid. This material was used in Step 3 without purification. LC-MS (Phenomenex 10 micromolar ("μm") C18 HPLC column: 3.0×50 mm length. Gradient: 100% Solvent A/0% Solvent B to 0% Solvent A 100% Solvent B. Gradient time: 3 min. Hold time: 1 min. Flow rate: 4 mL/min. Detector Wavelength: 220 nM. Solvent A: 10% MeOH/90% H₂O/0.1% TFA. Solvent B: 10% H₂O/90% MeOH/0.1% TFA. (Retention time: 2.50 min), MS m/z 313 (M⁺+1).

Step 3: Synthesis of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate

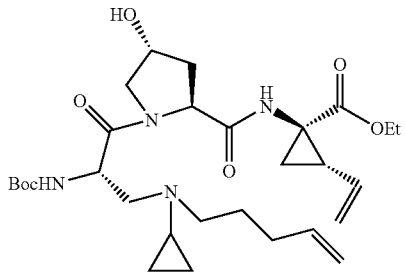

A solution of 2(S)-(tert-butoxycarbonylamino)-3-[N-cyclopropyl-N-(pent-4-enyl)amino]propanoic acid (1.47 g, 4.71 mmol.) in 20 mL of DCM was treated sequentially with ethyl 1(R)-[4(R)-hydroxypyrrolidine-2(S)-carboxamido]-2(S)-vinylcyclopropanecarboxylate hydrochloride (prepared in example 5) (1.44 g, 4.71 mmol.), N-methyl morpholine (1.80 mL, 16.34 mmol.), and HATU (2.14 g, 5.53 mmol.). The reaction mixture was stirred at rt under N₂ for 3 h, and then concentrated in vacuo. The residue was dissolved in water and 1N HCl was added until the pH=5. This aqueous solution was extracted with EtOAc (3×). The organic phase was washed with sat. aq. NaHCO₃, dried (MgSO₄), and concentrated in vacuo to give the crude product. Flash chromatography (50% ethyl acetate/hexane to 100% ethyl acetate) gave 1.55 g (58%) of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate as a white foam: LC-MS (Phenomenex-Luna S10 HPLC column: 3.0×50 mm length. Gradient: 100% Solvent A/0% Solvent B to 0% Solvent A/100% Solvent B. Gradient time: 2 min. Hold time: 1 min. Flow rate: 4 mL/min. Detector Wavelength: 220 nM. Solvent A: 10% MeOH/90% H₂O/0.1% TFA. Solvent B: 10% H₂O/90% MeOH/0.1% TFA.) (Retention time: 1.38 min), MS m/z 564 (M⁺+1).

Step 4: Synthesis of ethyl 1(R)-[1-[2(S)-(tert-butoxy-carbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate

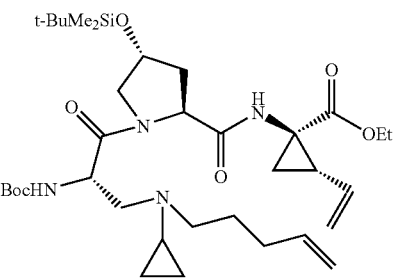

To a mixture of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate (1.55 g, 2.75 mmol.) in 10 mL of DMF was added imidazole (0.47 g, 6.88 mmol.) and tert-butyldimethylsilyl chloride (826 mg, 5.50 mmol.). The mixture was stirred at rt for 18 h, concentrated in vacuo, and partitioned between ethyl acetate and water. The organic phase was dried over magnesium sulfate, and concentrated in vacuo to obtain an off-white solid. Flash chromatography (eluting with methylene chloride and then ethyl acetate) gave ethyl 1(R)-[1-[2(S)-(tert-butoxycarbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate as a white solid (1.75 g, 94%): LC-MS (Phenomenex 10 μm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% H$_2$O/0.1% TFA. Solvent B: 10% H$_2$O/90% MeOH/0.1% TFA.) (Retention time: 2.51 min), MS m/z 677 (M$^+$+1).

Step 5: Synthesis of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid, ethyl ester

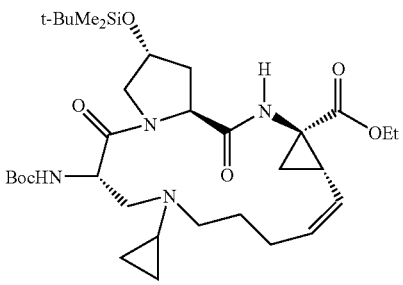

To a solution of ethyl 1(R)-[1-[2(S)-(tert-butoxycarbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate (1.45 g, 2.14 mmol.) in 1 L of methylene chloride was added 181 mg (0.21 mmol.) of Grubb's 2$^{nd}$ generation catalyst [(1,3-Bis-(2,4,6-trimethylphenyl)-2-imidazolidinylidene)dichloro(phenylmethylene)(tricyclohexylphosphine)ruthenium]. The mixture was heated at reflux for 1 h. A second fraction of the catalyst (50 mg, 0.058 mmol) was added, and the mixture was stirred at rt overnight. The residue was concentrated in vacuo, and then purified by flash chromatography eluting with 50% ether/hexane to give 0.84 g (62%) of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid, ethyl ester as a white solid: LC-MS (Phenomenex 10 μm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% H$_2$O/0.1% TFA. Solvent B: 10% H$_2$O/90% MeOH/0.1% TFA.) (Retention time: 2.43 min), MS m/z 649 (M$^+$+1).

Step 6: Synthesis of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid

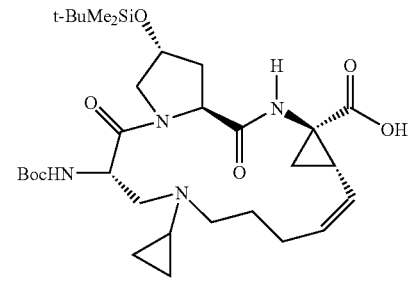

To a solution of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid, ethyl ester (0.84 g, 1.30 mmol.) in THF (30 mL), methanol (15 mL), and water (4 mL), was added powdered lithium hydroxide hydrate (0.31 g, 12.90 mmol.). The resultant light yellow slurry was stirred at rt under N$_2$ overnight. The mixture was then concentrated in vacuo, and partitioned between hexane/ether (1:1) and water. The organic phase was discarded, and the aqueous phase was treated with 1 N HCl until pH 5. This acidic solution was extracted with EtOAc (3×). The combined EtOAc extracts were dried (MgSO$_4$) and concentrated in vacuo to give 0.495 g (61%) of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid as an off-white solid: LC-MS (Phenomenex 10 μm C18 HPLC column: 3.0×50 mm length. Gradient: 100% Solvent A/0% Solvent B to 0% Solvent A 100% Solvent B. Gradient time: 2 min. Hold time: 1 min. Flow rate: 5 mL/min. Detector Wavelength: 220 nM. Solvent A: 10% MeOH/90% H$_2$O/0.1%

TFA. Solvent B: 10% H₂O/90% MeOH/0.1% TFA.) (Retention time: 2.36 min), MS m/z 621 (M⁺+1).

Step 7: Synthesis of (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl]carbamic acid, tert-butyl ester

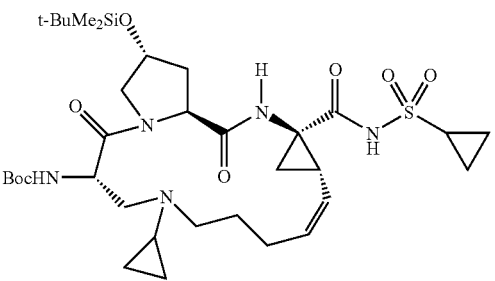

(1S,4R,6S,14S,18R)-7-cis-14-tert-Butoxycarbonylamino-18-(tert-butyldimethylsilyloxy)-2,15-dioxo-3,12,16-triazatricyclo[14.3.0.0⁴,⁶]nonadec-7-ene-4-carboxylic acid (490 mg, 0.79 mmol) was dissolved in 15 mL of THF and treated with CDI (179 mg, 1.10 mmol.). (Care was taken to avoid moisture by using oven dried glassware and maintaining a dry N₂ atmosphere.) After refluxing the reaction mixture for two hours, it was cooled to rt and treated sequentially with cyclopropylsulfonamide (134 mg, 1.10 mmol.) and DBU (168 mg, 1.10 mmol.). After stirring overnight at rt, the THF was removed by rotary evaporation. The residue was dissolved in water and 1N HCl was added until the pH=5. This aqueous solution was extracted with EtOAc (3×). The combined EtOAc extracts were dried (MgSO₄) and concentrated in vacuo to give the crude product. Purification by flash column, eluting with 3% methanol in methylene chloride, gave 300 mg (53%) of (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl]carbamic acid, tert-butyl ester as a white solid: LC-MS (Phenomenex 10 μm C18 HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% H₂O/ 0.1% TFA. Solvent B: 10% H₂O/90% MeOH/0.1% TFA.) (Retention time: 2.40 min), MS m/z 724 (M⁺+1).

Step 8: Synthesis of (1S,4R,6S,14S,18R)-[7-cis-4-Cyclopropanesulfonylaminocarbonyl-12-cyclopropyl-18-hydroxy-2,15-dioxo-3,12,16-triaza-tricyclo[14.3.0.0⁴,⁶]nonadec-7-en-14-yl]carbamic acid, tert-butyl ester (Example 86)

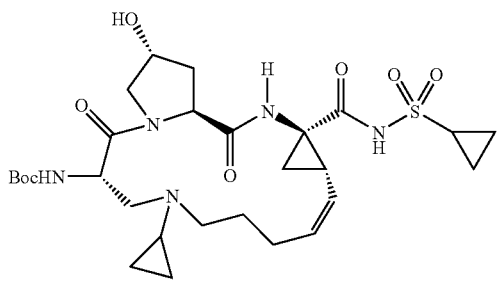

Example 86

To a mixture of compound (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl]carbamic acid, tert-butyl ester (250 mg, 0.35 mmol.) in 15 mL of THF was added tetrabutylammonium fluoride (129 mg, 0.46 mmol.). The mixture was stirred at rt for 18 h. THF was removed by rotary evaporation, and the residue was partitioned between ethyl acetate and water. The organic phase was dried (MgSO₄) and concentrated in vacuo to give the crude product. Purification by triturating with hexane provided 200 mg (94%) of (1S,4R, 6S,14S,18R)-[7-cis-4-Cyclopropanesulfonylaminocarbonyl-12-cyclopropyl-18-hydroxy-2,15-dioxo-3,12,16-triaza-tricyclo[14.3.0.0⁴,⁶]nonadec-7-en-14-yl]carbamic acid, tert-butyl ester as a white solid: LC-MS (retention time: 2.32 min), MS m/z 610 (M⁺+1). (Phenomenex 10 μm C18 HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nM. Solvent A: 10% MeOH/90% H₂O/ 0.1% TFA. Solvent B: 10% H₂O/90% MeOH/0.1% TFA.) (Retention time: 2.32 min), MS m/z 610 (M⁺+1).

Example 87

Preparation of Compound 1

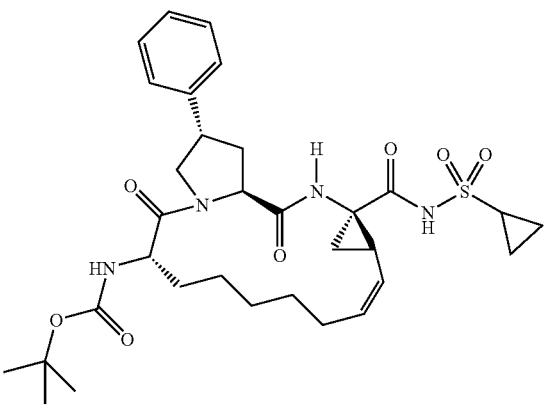

Compound 1

Scheme 1

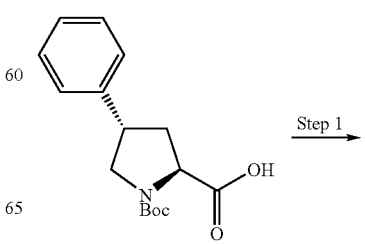

Step 1

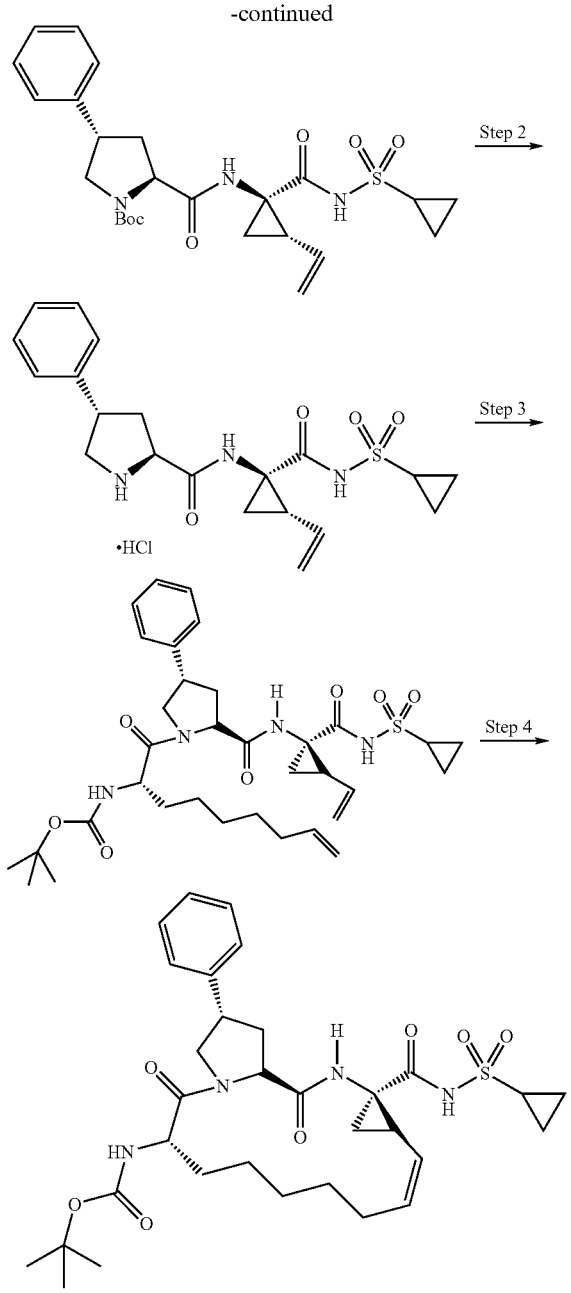

Step 1: Preparation of (2S,4S)-tert-butyl 2-((1R,2S)-1-(cyclopropylsulfonylcarbamoyl)-2-vinylcyclopropylcarbamoyl)-4-phenylpyrrolidine-1-carboxylate To a mixture of (2S,4S)-Boc-4-phenylpyrrolidine-2-carboxylic acid (0.711 g 2.44 mmol) (purchased from Chem-Impex International, Inc.), diisopropylethylamine (0.948 g, 7.33 mmol), and cyclopropanesulfonic acid (1-(R)-amino-2-(S)-vinyl-cyclopropanecarbonyl)amide HCl salt (0.561 g, 2.44 mmol) in dichloromethane (24 mL) was added HATU (1.21 g, 3.18 mmol). After stirring the reaction mixture for 14 hours, it was washed with 5% aqueous NaHCO₃ (50 mL), and 5% aqueous citric acid (50 mL). Each aqueous layer was sequentially extracted with 2×25 mL dichloromethane. The combined organic layer was dried over MgSO₄, filtered, and concentrated. The resulting brown viscous oil was purified by flash column chromatography (SiO₂, 97:3, dichloromethane:methanol) to give (2S,4S)-tert-butyl 2-((1R,2S)-1-(cyclopropylsulfonylcarbamoyl)-2-vinylcyclopropylcarbamoyl)-4-phenylpyrrolidine-1-carboxylate as a brown foamy solid (0.973 g, 79% yield). ¹H NMR (CD₃OD, 500 MHz) δ 0.91 (br s, 1H), 1.03 (d, J=6.4 Hz, 1H), 1.16-1.23 (m, 1H), 1.31-1.38 (m, 1H), 1.44 (dd, J=9.6, 5.6 Hz, 1H), 1.48 (s, 4H), 1.52 (s, 5H), 1.89 (t, J=6.4 Hz), 2.09 (q, J=8.4 Hz, 0.4H), 2.19 (q, J=8.6 Hz, 0.6H), 2.85-2.90 (m, 0.4H), 2.92-2.97 (m, 0.6H), 3.44 (t, J=9.6 Hz, 1H), 3.65 (p, J=8.0 Hz, 1H), 3.93-4.01 (m, 1H), 4.29 (dd, J=10.1, 6.7 Hz, 1H), 5.12 (d, J=10.1 Hz, 1H), 5.30 (d, J=18.0 Hz, 1H), 5.75-5.82 (m, 1H), 7.24 (t, J=6.9 Hz, 1H), 7.29-7.33 (m, 5H); MS m/z 504 (M+Na).

Step 2: Preparation of (2S,4S)—N-((1R,2S)-1-(cyclopropylsulfonylcarbamoyl)-2-vinylcyclopropyl)-4-phenylpyrrolidine-2-carboxamide To a solution of the product from Step 1, Example 1, (0.900 g, 1.79 mmol) in dichloromethane (5 mL) was added TFA (5 mL). After stirring at room temperature for 30 minutes, the reaction mixture was concentrated and dried under vacuum briefly. The resulting brown viscous oil was re-dissolved back into dichloromethane (10 mL) and was added dropwise to a solution of 1N HCl in diethyl ether (10 mL). A white solid precipitate formed and was collected by vacuum filtration. The filter cake was washed with diethyl ether to give 0.720 mg (91% yield) of (2S,4S)—N-((1R,2S)-1-(cyclopropylsulfonylcarbamoyl)-2-vinylcyclopropyl)-4-phenylpyrrolidine-2-carboxamide. MS m/z 404 (MH⁺).

Step 3: Preparation of tert-butyl(S)-1-((2S,4S)-2-((1R,2S)-1-(cyclopropylsulfonylcarbamoyl)-2-vinylcyclopropylcarbamoyl)-4-phenylpyrrolidin-1-yl)-1-oxonon-8-en-2-ylcarbamate To a solution of (S)-2-(tert-butoxycarbonylamino)non-8-enoic acid (purchased from RSP Amino Acids) (140 mg, 0.516 mmol) in 20 mL of DMF was added the product from Step 2, Example 1, (227 mg, 0.516 mmol). To this solution was added HATU (236 mg, 0.620 mmol) followed by N-methylmorpholine (182 mg, 1.80 mmol). The mixture was stirred at rt for 4 hours, and then was concentrated in vacuo to remove the DMF. The residue was partitioned between 0.1 N HCl and ethyl acetate (maintaining the aqueous phase between pH 3 to pH 5). The organic phase was dried (MgSO₄), filtered, and concentrated to give 300 mg of the crude product as a tan oil. Flash chromatography eluting with 1-5% methanol/CH₂Cl₂ gave 230 mg (68%) of tert-butyl(S)-1-((2S,4S)-2-((1R,2S)-1-(cyclopropylsulfonylcarbamoyl)-2-vinylcyclopropylcarbamoyl)-4-phenylpyrrolidin-1-yl)-1-oxonon-8-en-2-ylcarbamate as a colorless oil. MS m/z 657 (MH⁺).

Step 4: Preparation of Compound 1

The product of Step 3 (124 mg, 0.189 mmol) was dissolved in CH₂Cl₂, placed under an N₂ atmosphere, and treated with Grubb's 2ⁿᵈ generation RCM catalyst (tricyclohexylphosphine[1,3-bis(2,4,6-trimethyl-phenyl)-4,5-dihydroimidazol-2-ylidene][benzylidene]-ruthenium (IV) dichloride) (16 mg, 0.019 mmol). After refluxing for 18 hours, the orange/red solution was cooled to room temperature and concentrated in vacuo to give 125 mg of a brown oil. Flash chromatography eluting with 1-5% methanol/CH₂Cl₂ gave 60 mg of the crude macrocyclic product (~60% pure as estimated by ¹H NMR and LC/MS). Prep HPLC gave 22 mg of the pure product as an off-white solid. ¹H NMR (500 MHz, CDCl₃) δ ppm 0.90-1.00 (m, 1H), 1.05-1.14 (m, 1H), 1.14-1.22 (m, 1H), 1.23-1.84 (m, 10H), 1.41 (s, 9H), 1.88-2.00 (m, 2H), 2.14-2.29 (m, 2H), 2.39-2.49 (m, 1H), 2.50-2.60 (m, 1H), 2.86-2.96 (m, 1H), 3.91-4.01 (m, 2H), 4.05-4.14 (m, 1H), 4.39-4.48 (m, 1H), 4.48-4.56 (m, 1H), 4.97-5.04 (m, 1H), 5.13 (d, J=8.24 Hz, 1H), 5.70 (q, J=8.95 Hz, 1H), 6.72 (s, 1H), 7.36-7.24 (m, 5H), 10.14 (s, 1H). MS m/z 629 (MH$^+$).

Example 88

Preparation of Compound 2

Compound 2

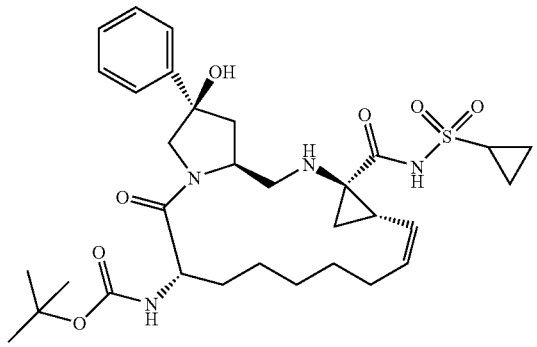

Step 1: Preparation of 1-(2(S)-tert-Butoxycarbonylamino-non-8-enoyl)-4(R)-hydroxy-pyrrolidine-2(S)-carboxylic acid methyl ester

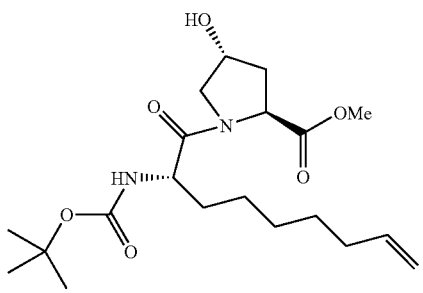

A solution of 2(S)-tert-butoxycarbonylamino-8-nonenoic acid (purchased from RSP Amino Acids) (3.5 g, 12.9 mmol) in 200 mL of dichloromethane was treated sequentially with 4(R)-hydroxypyrrolidine-2(S)-carboxylic acid methyl ester hydrochloride (2.15 g, 11.8 mmol), N-methyl morpholine (4.25 mL, 38.6 mmol), and HATU (5.37 g, 14.1 mmol). The reaction mixture was stirred at room temperature under N$_2$ for 3 days, and then concentrated in vacuo. The residue was partitioned between ethyl acetate and pH 4 buffer (biphthalate). The organic phase was washed with saturated aqueous NaHCO$_3$, dried (MgSO$_4$), filtered, and concentrated in vacuo to give the crude product. Flash chromatography (50% ethyl acetate/hexane to 100% ethyl acetate) gave 4.7 g (~100%) of 1-(2(S)-tert-butoxycarbonylamino-non-8-enoyl)-4(R)-hydroxy-pyrrolidine-2(S)-carboxylic acid methyl ester as a colorless oil. $^1$H NMR (500 MHz, CD$_3$OD) δ 1.33-1.50 (m, 8H), 1.46 (s, 9H), 1.57 (m, 1H), 1.72 (m, 1H) 2.08 (m, 2H), 2.28 (m, 1H), 3.72 (s, 3H,) 3.75-3.87 (m, 2H), 4.36 (m, 1H), 4.51 (bs, 1H), 4.57 (t, J=8.2 Hz, 1H), 4.95 (d, J=10.4 Hz, 1H), 5.01 (m, 1H), 5.83 (m, 1H); LC-MS (Method A, retention time: 3.01 min), MS m/z 399 (M$^+$+1).

Step 2: Preparation of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester

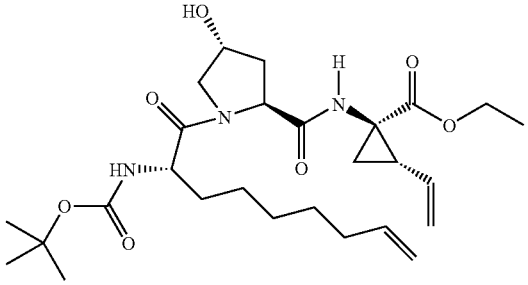

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at room temperature under N$_2$ for 16 hours, and then concentrated in vacuo. The residue was partioned between ether and water. The ether phase was discarded, and the aqueous phase was treated with 1N HCl until the pH was 4. This acidic solution was extracted with ethyl acetate (3×). The combined ethyl acetate extracts were dried (MgSO$_4$), filtered, and concentrated in vacuo to give 4.36 g (96%) of 1-(2(S)-tert-butoxycarbonylamino-8-nonenoyl)-4(R)-hydroxy-pyrrolidine-2(S)-carboxylic acid as a white solid. This acid was then dissolved in 150 mL of DMF and (1R,2S)-1-amino-2-vinyl-cyclopropane carboxylic acid ethyl ester hydrochloride (2.61 g, 13.6 mmol), N-methyl morpholine (2.5 mL, 22.6 mmol), and HATU (5.2 g, 13.7 mmol) was added. The reaction mixture was stirred at room temperature under N$_2$ for 16 hours, and then concentrated in vacuo. The residue was partitioned between ethyl acetate and pH 4 buffer (biphthalate). The organic phase was washed with saturated aqueous NaHCO$_3$, dried (MgSO$_4$), filtered, and concentrated in vacuo to give the crude product. Flash chromatography (60%-80% ethyl acetate/hexane) gave 6.0 g (98%) of 1-{[1-(2(S)-tert-butoxycarbonylamino-non-8-enoyl)-4(R)-hydroxy-pyrrolidine-2 (S)carbonyl]-(1R)-amino}-2(S)-vinyl-cyclopropanecarboxylic acid ethyl ester as a white solid. $^1$H NMR (500 MHz, CD$_3$OD) δ 1.25 (t, J=7.2 Hz, 3H), 1.33-1.80 (m, 10H), 1.46 (s, 9H), 2.09 (m, 3H), 2.25 (m, 2H), 3.76 (m, 2H), 4.14 (m, 2H), 4.27 (dd, J=8.5, 5.2 Hz, 1H), 4.50 (m, 2H), 4.94 (d, J=10.1 Hz, 1H), 5.01 (dd, J=17.1, 1.8 Hz, 1H), 5.11 (dd, J=10.4, 1.8 Hz, 1H), 5.30 (d, J=15.6 Hz, 1H), 5.80 (m, 2H), 8.57 (s, 1H); LC-MS (Method A, retention time: 3.21 min), MS m/z 522 (M$^+$+1).

Step 3: Preparation of 1-{[1-(2-tert-Butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester

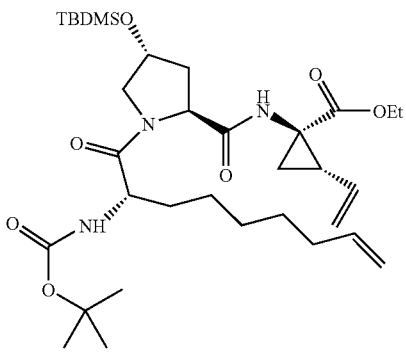

To a mixture of 1-{[1-(2(S)-tert-butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester (1.5 g, 2.87 mmol) in 10 mL of DMF was added imidazole (0.25 g, 3.67 mmol) and tert-butyl-dimethylsilyl chloride (516 mg, 3.44 mmol). The mixture was stirred at room temperature for two days. The reaction mixture was then concentrated in vacuo, and the residue was dissolved in ethyl acetate. This solution was washed with water, dried over magnesium sulfate, filtered, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester as a white solid. $^1$H NMR (300 MHz, CD$_3$OD) δ 0.10 (s, 6H), 0.89 (s, 9H), 1.22 (m, 3H), 1.31-1.48 (m, 16H), 1.50-1.75 (m, 3H), 2.06 (m, 3H), 2.11-2.33 (m, 2H), 3.70 (m, 2H), 4.03-4.19 (m, 2H), 4.21 (m, 1H), 4.45 (t, J=7.87 Hz, 1H), 4.59 (m, 1H), 4.91 (d, J=9.15 Hz, 1H), 4.98 (d, J=17.20 Hz, 1H), 5.08 (dd, J=10.25, 1.83 Hz, 1H), 5.27 (dd, J=17.38, 1.65 Hz, 1H), 5.65-5.87 (m, 2H). LC-MS (Method A, retention time: 4.00 min); MS m/z 636 (M$^+$+1).

Step 4: Preparation of 14-tert-Butoxycarbonylamino-18-(tert-butyl-dimethyl-silanyloxy)-2,15-dioxo-3,16-diaza-tricyclo[14.3.0.0$^{1,6}$]nonadec-7-ene-4-carboxylic acid, ethyl ester

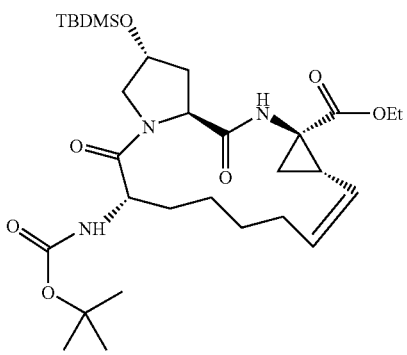

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmol) in 640 mL of methylene chloride was added 215 mg (0.26 mmol) of tricyclohexylphosphine[1,3-bis(2,4,6-tri[benzylidene]ruthenium(IV) dichloride. The mixture was heated at reflux for 15 minutes. The residue was concentrated in vacuo, and then purified by flash column chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester as a white solid. $^1$H NMR (500 MHz, CD$_3$Cl) δ 0.06 (s, 3H), 0.07 (s, 3H), 0.86 (s, 9H), 1.18-1.24 (m, 6H), 1.34-1.64 (m, 14H), 1.86-1.96 (m, 3H), 2.02-2.09 (m, 1H), 2.11-2.17 (m, 1H), 2.19-2.28 (m, 1H), 2.57-2.63 (m, 1H), 3.50-3.54 (m, 1H), 3.71 (dd, J=10.22, 6.26 Hz, 1H), 4.06-4.17 (m, 2H), 4.52-4.58 (m, 2H), 4.75 (d, J=8.55 Hz, 1H), 5.21 (t, J=9.92 Hz, 1H), 5.35 (d, J=7.63 Hz, 1H), 5.45-5.50 (m, 1H), 6.94 (s, 1H); LC-MS (Method A, retention time: 3.88 min), MS m/z 608 (M$^+$+1).

Step 5: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid

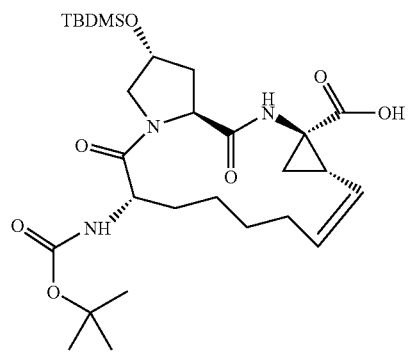

To a solution of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester (1.5 g, 2.47 mmol) in a mixed solvent system of THF (4 mL), methanol (1 mL), and water (2 mL), was added powdered lithium hydroxide monohydrate (1.0 g, 50 mmol). The light yellow slurry was stirred at rt under N$_2$ for 4 hours. The mixture was then concentrated in vacuo, and the residue partioned between ether and water. The ether phase was discarded, and the aqueous phase was treated with 1 N HCl until reaching pH 4. This acidic solution was extracted with ethyl acetate (3×). The combined ethyl acetate extracts were dried (MgSO$_4$), filtered, and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid as an off-white solid. $^1$H NMR (300 MHz, CD$_3$OD) 0.12 (s, 6H), 0.89 (s, 9H), 1.23-1.64 (m, 17H), 1.70-1.87 (m, 1H), 1.90-2.49 (m, 6H), 3.70-3.80 (m, 1H), 3.83-3.90 (m, 1H), 4.28-4.36 (m, 1H), 4.47-4.55 (m, 1H), 4.65 (s, 1H), 5.30-5.39 (m, 1H), 5.53-5.62 (m, 1H); LC-MS (Method A, retention time: 3.69 min), MS m/z 580 (M$^+$+1).

Step 6: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butylester

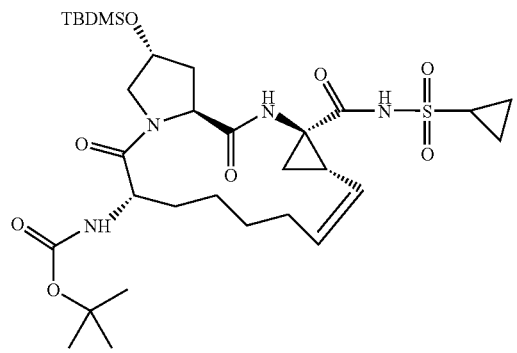

14-tert-Butoxycarbonylamino-18-(tert-butyl-dimethyl-silanyloxy)-2,15-dioxo-3,16-diaza-tricyclo[14.3.0.0^{4,6}]nonadec-7-ene-4-carboxylic acid (500 mg, 0.86 mmol) was dissolved in 25 mL of THF and treated with CDI (180 mg, 1.12 mmol) (care was taken to avoid moisture by using oven dried glassware and maintaining a dry $N_2$ atmosphere). After refluxing the reaction mixture for 2 hours, it was cooled to room temperature and treated sequentially with cyclopropylsulfonamide (135 mg, 1.12 mmol) and DBU (170 mg, 1.12 mmol). The reaction mixture was stirred for 4 hours at room temperature, and the THF was removed by rotary evaporation. The residue was partitioned between ethyl acetate and pH 4 buffer. The organic phase was dried ($MgSO_4$), filtered, and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.0^{4,6}]nonadec-7-en-14-yl]-carbamic acid tert-butyl ester as a white solid. $^1$H NMR (300 MHz, $CD_3OD$) δ 0.07 (s, 3H), 0.08 (s, 3H), 0.85 (s, 9H), 0.87-1.49 (m, 21H), 1.73-1.95 (m, 3H), 2.08-2.16 (m, 1H), 2.25-2.36 (m, 2H), 2.42-2.56 (m, 1H), 2.85-2.93 (m, 1H), 3.65-3.74 (dd, J=10.61, 3.66 Hz, 1H), 3.89 (d, J=10.25 Hz, 1H), 4.34 (m, J=9.70, 9.70 Hz, 1H), 4.43 (t, J=7.87 Hz, 1H), 4.57 (s, 1H), 4.94-5.01 (m, 1H), 5.10 (d, J=8.78 Hz, 1H), 5.66-5.75 (m, 1H), 6.55 (s, 1H), 10.13 (s, 1H); LC-MS (Method A, retention time: 3.81 min), MS m/z 683 ($M^+$+1).

Step 7: Preparation of (4-Cyclopropanesulfonylaminocarbonyl-18-hydroxy-2,15-dioxo-3,16-diaza-tricyclo[14.3.0.0^{4,6}]nonadec-7-en-14-yl)-carbamic acid tert-butyl ester

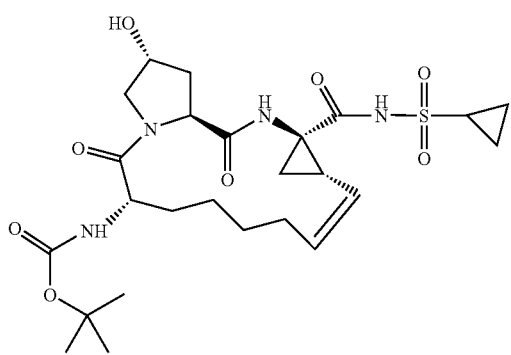

To a mixture of [18-(tert-butyl-dimethylsilanyloxy)-4-cyclopropanesulfonylaminocarbonyl-2,15-dioxo-3,16-diazatricyclo[14.3.0.0^{4,6}]nonadec-7-en-14-yl]-carbamic acid tert-butyl ester (330 mg, 0.48 mmol) in 25 mL of THF was added tetrabutylammonium fluoride (150 mg, 0.54 mmol). The reaction mixture was stirred at room temperature for 18 hours, and then the THF was removed by rotary evaporation. The residue was partitioned between ethyl acetate and water. The organic phase was dried ($MgSO_4$), filtered, and concentrated in vacuo to give the crude product. It was then purified by triturating with hexane to yield 200 mg (73%) of (4-cyclopropanesulfonylaminocarbonyl-18-hydroxy-2,15-dioxo-3,16-diaza-tricyclo[14.3.0.0^{4,6}]nonadec-7-en-14-yl)-carbamic acid tert-butyl ester as a white solid. $^1$H NMR (500 MHz, $CD_3Cl$) δ 1.87-1.64 (m, 21H), 1.70-1.98 (m, 3H), 2.15-2.56 (m, 5H), 2.85-2.94 (m, 1H), 3.71 (d, J=13.91 Hz, 1H), 4.10-4.26 (m, 2H), 4.51 (t, J=7.87 Hz, 1H), 4.62 (s, 1H), 4.98 (m, 1H), 5.06 (d, J=8.78 Hz, 1H), 5.64-5.71 (m, 1H), 6.72 (s, 1H), 10.24 (s, 1H); LC-MS (Method A, retention time: 2.85 min), MS m/z 569 ($M^+$+1).

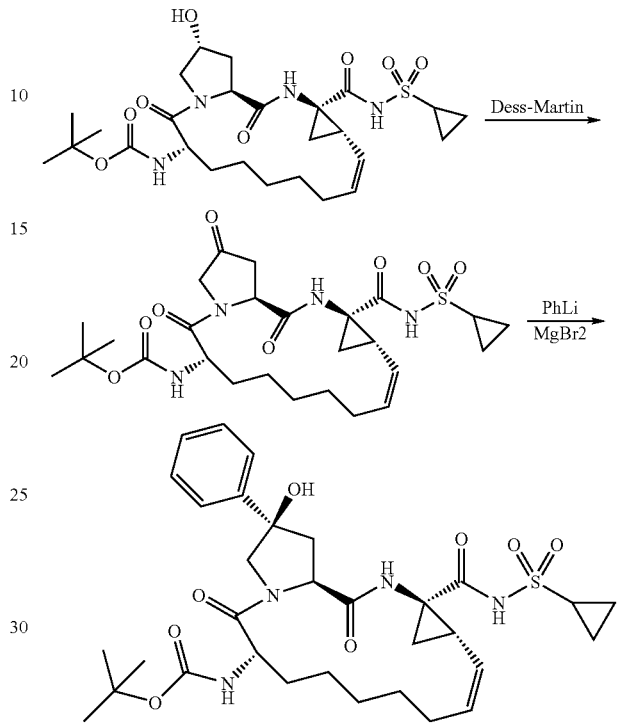

Step 8:

To a solution of (4-cyclopropanesulfonylaminocarbonyl-18-hydroxy-2,15-dioxo-3,16-diaza-tricyclo[14.3.0.0^{4,6}]nonadec-7-en-14-yl)-carbamic acid tert-butyl ester (1.00 g, 1.76 mmol) in dichloromethane (50 mL) was added Dess-Martin reagent (1.64 g, 3.87 mmol) as solid by one portion at 0° C. After removal of ice bath, the mixture was stirred at room temperature for 3 hours, quenched with 2-propanol (2 mL), stirred for an additional 1 hour, and concentrated in vacuo. The residue was triturated with ethyl acetate, and filtered, and the filtrate was concentrated. The residue was triturated with dichloromethane and filtered. The filtrate was concentrated to dryness. The residue was purified by flash column, eluted with first 2:1, then 1:1 hexane-acetone to yield the desired product as white solid (670 mg, 67%). LC-MS (retention time: 2.42 min, method B), MS m/z 567 ($M^+$+H).

Step 9:

A 2-necked flask containing magnesium bromide diethyl etherate (183 mg, 0.71 mmol) was heated in an oil bath at 70° C. for 4 hours under high vacuum. After cooling to room temperature, tert-butyl (6S,13aS,14aR,16aS,Z)-14a-(cyclopropylsulfonylcarbamoyl)-2,5,16-trioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (40 mg, 0.071 mmol) was charged in. Cooled the flask with ice. Anhydrous THF (2 mL) was added via syringe. The formed slightly yellow slurry was vigorously stirred at room temperature overnight. To this flask cooled with dry ice-acetone was added phenyl lithium (1.8 M in THF, 0.39 mL, 0.71 mmol) dropwise. The mixture was stirred at this temperature for 2 hours before the bath was replaced with an ice bath and stirred for another 1 hour. The mixture was quenched with saturated NH₄Cl, and extracted with ethyl acetate. The separated organic layer was washed with brine, dried over MgSO₄, filtered, and concentrated. The residue was triturated with hexane (5 mL), and filtered. The filtrate was concentrated and purified by prep-HPLC to afford 9.5 mg (21%) of the desired product as a white solid. $^1$H NMR (CD₃OD) δ 1.01-1.21 (m, 4H), 1.28-1.39 (m, 2H), 1.45 (s, 9H), 1.49-1.52 (m, 4H), 1.63-1.72 (m, 2H), 1.80-1.91 (m, 2H), 1.98-2.04 (m, 1H), 2.30-2.35 (m, 1H), 2.44-2.55 (m, 2H), 2.70-2.74 (m, 1H), 2.94-2.97 (m, 1H), 4.06-4.08 (m, 1H), 4.31-4.39 (m, 2H), 4.60-4.63 (m, 1H), 5.21-5.29 (m, 1H), 5.65-5.71 (m, 1H), 7.31-7.34 (m, 1H), 7.38-7.42 (m, 2H), 7.63-7.65 (m, 2H); LC-MS (retention time: 2.74 min, method B), MS m/z 627 (M⁺+H—H₂O), 571 (M⁺+H—H₂O-t-Butyl).

Example 89

Preparation of Compound 3

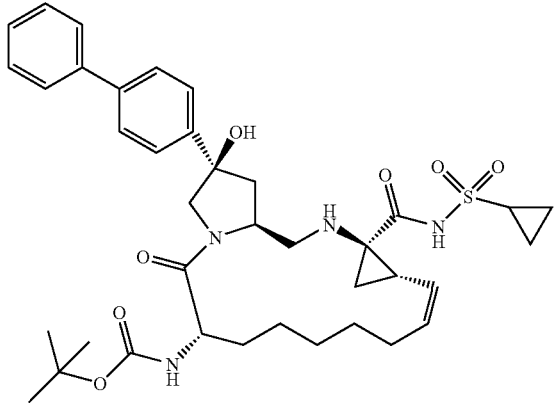

Compound 3

Compound 3 was made using the same method of Compound 2. A 2-necked flask (Flask A) containing magnesium bromide diethyl etherate (183 mg, 0.71 mmol) was heated in an oil bath at 70° C. for 4 hours under high vacuum. After cooling to room temperature, tert-butyl (6S,13aS,14aR,16aS, Z)-14a-(cyclopropylsulfonylcarbamoyl)-2,5,16-trioxo-1,2, 3,5,6,7,8,9,10,11,13a,14,14a,15,16,16a-hexadecahydrocyclopropa[e]pyrrolo[1,2-a][1,4]diazacyclopentadecin-6-ylcarbamate (40 mg, 0.071 mmol) was added. The flask was cooled with ice. Anhydrous THF (2 mL) was added via syringe. The formed slightly yellow slurry was vigorously stirred at room temperature overnight.

To another 2-necked flask (Flask B) containing a solution of 4-bromobiphenyl (165 mg, 0.71 mmol) in THF (4 mL) at −78° C. was added n-BuLi (2.5 M in hexane, 0.28 mL, 0.71 mmol) dropwise and the formed solution was stirred at this temperature for 1 hour.

The content of Flask B at −78° C. was transferred to Flask A cooled to −78° C. via cannula. The formed yellowish solution was stirred at this temperature for 2 hours before the dry-acetone bath was replaced with an ice bath and stirred for another 1 hour. The mixture was quenched with NH₄Cl (sat.), and extracted with ethyl acetate. The separated organic layer was washed with brine, dried over MgSO₄, filtered, and concentrated. The residue was triturated with hexane (5 mL), and filtered. The filtrate was concentrated and purified by prep-HPLC to afford 4.1 mg (8%) of the desired product as a white solid. $^1$H NMR (CD₃OD) δ 0.87-1.10 (m, 4H), 1.24-1.38 (m, 2H), 1.45 (s, 9H), 1.49-1.52 (m, 4H), 1.70-1.84 (m, 4H), 1.99-2.10 (m, 1H), 2.22-2.35 (m, 1H), 2.40-2.60 (m, 2H), 2.70-2.80 (m, 1H), 2.90-2.99 (m, 1H), 4.08-4.11 (m, 1H), 4.31-4.41 (m, 2H), 4.61-4.69 (m, 1H), 5.23-5.32 (m, 1H), 5.61-5.70 (m, 1H), 7.35-7.38 (m, 1H), 7.43-7.48 (m, 2H), 7.62-7.70 (m, 6H); LC-MS (retention time: 2.74 min, method B), MS m/z 703 (M⁺+H—H₂O), 647 (M⁺+H—H₂O-t-Butyl).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol.

72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride ($MgCl_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultracentrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET SI (Resonance Energy Transfer Depsipeptide Substrate; AnaSpec, Inc. cat #22991) (FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 μM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 μM depending on their potency. The enzyme assays were each initiated by addition of substrate to enzyme-inhibitor pre-incubated for 10 min at room temperature and hydrolysis to 15% conversion as measured on cytofluor.

The final conditions for each assay were as follows:
50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 μM LLVY-AMC and 1 nM Chymotrypsin.

50 mM Tris-HCl, pH 8.0, 50 mM NaCl, 0.1 mM EDTA, 3% DMSO, 0.02% Tween-20, 5 μM succ-AAPV-AMC and 20 nM HNE or 8 nM PPE;

100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 μM Z-FR-AMC diluted in H$_2$O.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration (IC$_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Accession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before (1.5×10$^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a CC$_{50}$ reading. The toxicity of compound (CC$_{50}$) was determined by adding $\frac{1}{10}^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 μl). The cells were lysed with 25 μl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 μM final from a 2 mM stock in 100% DMSO. The plate was then placed into the Cytofluor 4000 instrument which had been set to 340 nm excitation/490 nm emission, automatic mode for 21 cycles and the plate read in a kinetic mode. EC$_{50}$ determinations were carried out as described for the IC$_{50}$ determinations.

HCV Replicon Luciferase Reporter Assay

As a secondary assay, EC$_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the *Renilla luciferase* gene and a linker sequence fused directly to the 3'-end of the luciferase gene. This insert was introduced into the replicon construct using an AscI restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% CO$_2$ incubator, cells were analyzed for *Renilla Luciferase* activity using the Promega Dual-Glo Luciferase Assay System. Media (100 μl) was removed from each well containing cells. To the remaining 50 μl of media, 50 μl of Dual-Glo Luciferase Reagent was added, and plates rocked for 10 min to 2 h at room temperature. Dual-Glo Stop & Glo Reagent (50 μl) was then added to each well, and plates were rocked again for an additional 10 min to 2 h at room temperature. Plates were read on a Packard TopCount NXT using a luminescence program.

The percentage inhibition was calculated using the formula below:

% control=average luciferase signal in experimental
wells(+compound)/average luciferase signal in
DMSO control wells(−compound)

The values were graphed and analyzed using XLfit to obtain the EC$_{50}$ value.

Note that by using the patent example number and the patent compound number shown in Table 2 the structures of compounds can be found herein.

TABLE 2

| Example Number | Compound Number | IC50 (nM) | EC50 (nM) |
| --- | --- | --- | --- |
| 87 | 1 | 18 | 639 |
| 88 | 2 | 9 | 389 |
| 89 | 3 | 2 | 14 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

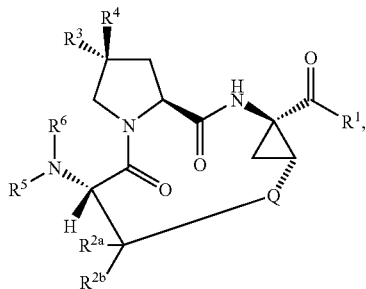

or a pharmaceutically acceptable salt thereof, wherein $R^1$ is selected from alkoxy, hydroxy, and —NHSO$_2$R$^7$;

$R^{2a}$ and $R^{2b}$ are independently selected from hydrogen and methyl;

$R^3$ is selected from alkenyl, alkyl, aryl, arylalkyl, cycloalkyl, (cycloalkyl)alkyl, heterocyclyl, and heterocyclylalkyl; provided that when $R^4$ is hydrogen then $R^3$ is other than heterocyclyl;

$R^4$ is selected from hydrogen and hydroxy;

$R^5$ is selected from hydrogen, alkyl, and cycloalkyl;

$R^6$ is selected from hydrogen, alkyl, alkoxycarbonyl, alkylaminocarbonyl, alkylcarbonyl, aminocarbonyl, aryloxycarbonyl, cycloalkyloxycarbonyl, dialkylaminocarbonyl, haloalkoxycarbonyl, haloalkyl, haloalkylcarbonyl, heterocyclyloxycarbonyl, and (NR$^a$R$^b$)sulfonyl;

$R^7$ is selected from alkyl, aryl, cycloalkyl, (cycloalkyl)alkyl, heterocyclyl, and —NR$^a$R$^b$; wherein the cycloalkyl and the cycloalkyl part of the (cycloalkyl)alkyl are optionally substituted with one, two, or three groups independently selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and (NR$^e$R$^f$)carbonyl; and wherein R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl; and wherein R$^e$ and R$^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo; and Q is a C$_{3-9}$ saturated or unsaturated chain, optionally containing one to three heteroatoms independently selected from O, S(O)$_m$, and NR$^9$, wherein m is 0, 1, or 2, and R$^9$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkyloxy, dialkylaminocarbonyl, dialkylaminocarbonylalkyl, haloalkyl, and heterocyclylcarbonyl.

2. A compound of claim 1, or a pharmaceutically acceptable salt thereof, wherein R$^4$ is hydroxy.

3. A compound of claim 1, or a pharmaceutically acceptable salt thereof, wherein R$^1$ is —NHSO$_2$R$^7$.

4. A compound of claim 3, or a pharmaceutically acceptable salt thereof, wherein R$^7$ is cycloalkyl.

5. A compound of claim 1, or a pharmaceutically acceptable salt thereof, wherein R$^{2a}$ and R$^{2b}$ are hydrogen.

6. A compound of claim 1, or a pharmaceutically acceptable salt thereof, wherein Q is a C$_{5-7}$ unsaturated chain containing zero heteroatoms.

7. A compound of claim 6, or a pharmaceutically acceptable salt thereof, wherein Q is a C$_6$ unsaturated chain containing zero heteroatoms.

8. A compound of formula (II)

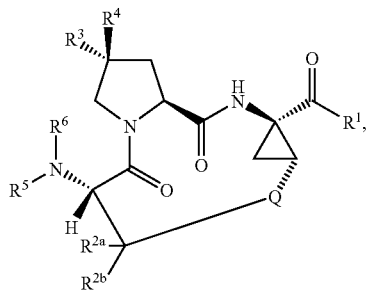

or a pharmaceutically acceptable salt thereof, wherein $R^1$ is —NHSO$_2$R$^7$;

$R^{2a}$ and $R^{2b}$ are hydrogen;

$R^3$ is selected from alkenyl, alkyl, aryl, arylalkyl, cycloalkyl, (cycloalkyl)alkyl, heterocyclyl, and heterocyclylalkyl; provided that when $R^4$ is hydrogen then $R^3$ is other than heterocyclyl;

$R^4$ is selected from hydrogen and hydroxy;

$R^5$ is hydrogen;

$R^6$ is alkoxycarbonyl;

$R^7$ is selected from alkyl, aryl, cycloalkyl, (cycloalkyl)alkyl, heterocyclyl, and —NR$^a$R$^b$; wherein R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl; and Q is a C$_{3-9}$ saturated or unsaturated chain, optionally containing one to three heteroatoms independently selected from O, S(O)$_m$, and NR$^9$, wherein m is 0, 1, or 2, and R$^9$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkyloxy, dialkylaminocarbonyl, dialkylaminocarbonylalkyl, haloalkyl, and heterocyclylcarbonyl.

9. A compound of claim 8, or a pharmaceutically acceptable salt thereof, wherein R$^4$ is hydroxy.

10. A compound of claim 8, or a pharmaceutically acceptable salt thereof, wherein R$^7$ is cycloalkyl.

11. A compound of claim 8, or a pharmaceutically acceptable salt thereof, wherein Q is a C$_6$ unsaturated chain containing zero heteroatoms.

12. A compound selected from

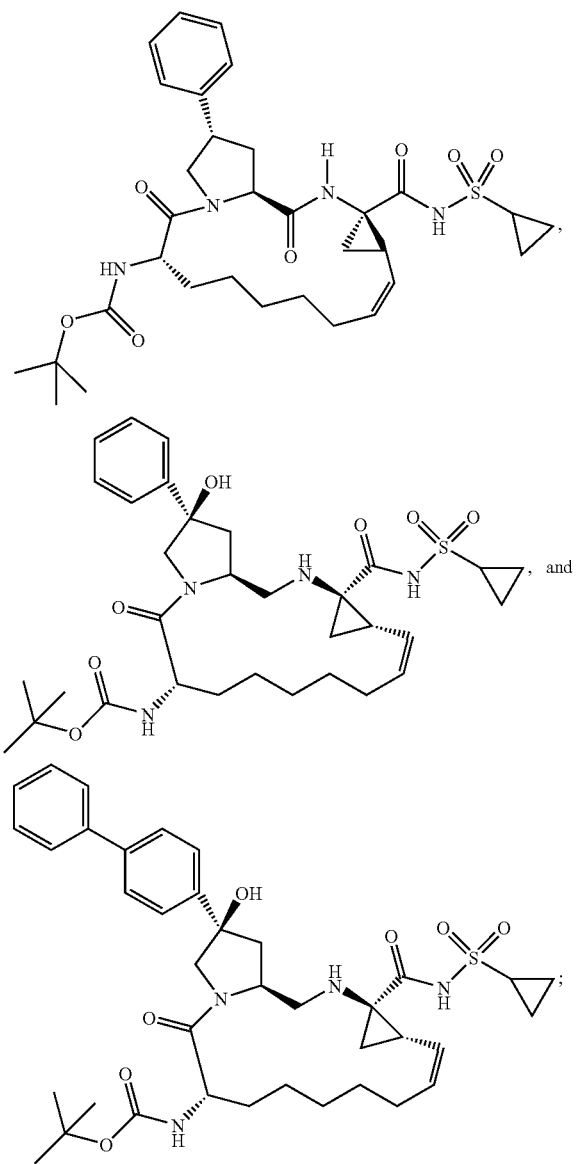

or a pharmaceutically acceptable salt thereof.

13. A composition comprising the compound of claim 1, or a pharmaceutically acceptable salt thereof, and a pharmaceutically acceptable carrier.

14. The composition of claim 13 further comprising at least one additional compound having anti-HCV activity.

15. The composition of claim 14 wherein at least one of the additional compounds is an interferon or a ribavirin.

16. The composition of claim 15 wherein the interferon is selected from interferon alpha 2B, pegylated interferon alpha, consensus interferon, interferon alpha 2A, and lymphoblastiod interferon tau.

17. The composition of claim 14 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

18. The composition of claim 14 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

19. A method of treating an HCV infection in a patient, comprising administering to the patient a therapeutically effective amount of a compound Formula (I) of claim 1, or a pharmaceutically acceptable salt thereof.

20. The method of claim 19 further comprising administering at least one additional compounds having anti-HCV activity prior to, after, or simultaneously with the compound of Formula (I), or a pharmaceutically acceptable salt thereof.

21. The method of claim 20 wherein at least one of the additional compounds is an interferon or a ribavirin.

22. The method of claim 21 wherein the interferon is selected from interferon alpha 2B, pegylated interferon alpha, consensus interferon, interferon alpha 2A, and lymphoblastiod interferon tau.

23. The method of claim 20 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

24. The method of claim 20 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,003,604 B2  Page 1 of 1
APPLICATION NO. : 11/939753
DATED : August 23, 2011
INVENTOR(S) : Alan Xiangdong Wang et al.

It is certified that error appears in the above-identified patent and that said Letters Patent is hereby corrected as shown below:

In the Specification:

Column 4, line 59, change "lymphoblastiod" to -- lymphoblastoid --.

Column 5, line 1, change "Imiqimod" to -- Imiquimod --.

Column 5, line 2, change "5′-monophospate" to -- 5′-monophosphate --.

Column 5, line 27, change "lymphoblastiod" to -- lymphoblastoid --.

Column 5, line 40, change "Imiqimod" to -- Imiquimod --.

Column 5, line 41, change "5′-monophospate" to -- 5′-monophosphate --.

Signed and Sealed this
Twenty-fifth Day of September, 2012

David J. Kappos
*Director of the United States Patent and Trademark Office*